US009387349B2

(12) United States Patent
Loy et al.

(10) Patent No.: US 9,387,349 B2
(45) Date of Patent: Jul. 12, 2016

(54) **COMPOSITIONS COMPRISING *PAULOWNIA TOMENTOSA* WOOD EXTRACTS AND USES THEREOF**

(75) Inventors: Chong Jin Loy, Singapore (SG); Khalid Mahmood, South Hadley, MA (US); Claude Saliou, Basking Ridge, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 661 days.

(21) Appl. No.: 12/859,322

(22) Filed: Aug. 19, 2010

(65) Prior Publication Data

US 2012/0045491 A1 Feb. 23, 2012

(51) Int. Cl.
*A61Q 19/02* (2006.01)
*A61K 8/97* (2006.01)

(52) U.S. Cl.
CPC .. *A61Q 19/02* (2013.01); *A61K 8/97* (2013.01)

(58) Field of Classification Search
None
See application file for complete search history.

(56) References Cited

U.S. PATENT DOCUMENTS

| | | | |
|---|---|---|---|
| 4,337,370 | A | 6/1982 | Takisawa et al. |
| 4,795,638 | A | 1/1989 | Ayache et al. |
| 5,674,497 | A | 10/1997 | Kuwana |
| 6,410,062 | B1 | 6/2002 | Callaghan et al. |
| 7,235,266 | B2 | 6/2007 | Park |
| 7,252,844 | B2 | 8/2007 | Park |
| 7,442,391 | B2 | 10/2008 | Koganov |
| 7,473,435 | B2 | 1/2009 | Koganov |
| 7,537,791 | B2 | 5/2009 | Koganov |
| 8,853,264 | B2 | 10/2014 | Hwang et al. |
| 2005/0226834 | A1 | 10/2005 | Lambino et al. |
| 2006/0083707 | A1 | 4/2006 | Park |
| 2006/0105058 | A1 | 5/2006 | Park |
| 2006/0141014 | A1 | 6/2006 | Eknoian et al. |
| 2006/0275229 | A1 | 12/2006 | Pillai et al. |
| 2007/0042010 | A1 | 2/2007 | Southall et al. |
| 2007/0196523 | A1 | 8/2007 | Koganov |
| 2008/0095719 | A1 | 4/2008 | Herrmann et al. |
| 2009/0075946 | A1 | 3/2009 | Ochiai et al. |
| 2009/0241242 | A1 | 10/2009 | Beatty et al. |
| 2010/0215785 | A1 | 8/2010 | Kizoulis et al. |
| 2011/0118346 | A1 | 5/2011 | Hwang et al. |

FOREIGN PATENT DOCUMENTS

| | | | |
|---|---|---|---|
| CN | 1103284 | A | 6/1995 |
| CN | 1453289 | A | 11/2003 |
| CN | 1673332 | A | 9/2005 |
| CN | 1699398 | A | 11/2005 |
| CN | 101102761 | A | 1/2006 |
| CN | 1768728 | A | 5/2006 |
| CN | 1875786 | A | 12/2006 |
| CN | 100998680 | A | 7/2007 |
| CN | 101205248 | A | 6/2008 |
| CN | 101293014 | A | 10/2008 |
| CN | 101618114 | A | 1/2010 |
| CN | 101618154 | A | 1/2010 |
| CN | 101827579 | B | 1/2013 |
| DE | 10238449 | | 3/2004 |
| EP | 1327438 | A | 7/2003 |
| EP | 1698325 | A | 9/2006 |
| EP | 1775306 | B1 | 4/2009 |
| FR | 575342 | | 9/1923 |
| FR | 2885804 | A | 11/2006 |
| JP | 58057307 | A | 4/1983 |
| JP | 60246305 | | 12/1985 |
| JP | 61212518 | A | 9/1986 |
| JP | 62108804 | A | 5/1987 |
| JP | 03190809 | A | * 8/1991 |
| JP | 7309770 | | 11/1995 |
| JP | 7330554 | | 12/1995 |
| JP | 7330554 | A | 12/1995 |
| JP | 7330555 | | 12/1995 |
| JP | 8157347 | A | 6/1996 |
| JP | 9077636 | A | 3/1997 |
| JP | 2002265324 | A | 9/2002 |
| JP | 2005008572 | A | 1/2005 |
| JP | 2005082522 | A | * 3/2005 |
| JP | 2006124335 | A | 5/2006 |
| JP | 2006335698 | A | 12/2006 |
| KR | 165564 | B1 | 1/1999 |
| KR | 20010044451 | A | 6/2001 |
| KR | 20020083094 | A | 11/2002 |
| KR | 20030037992 | A | 5/2003 |
| KR | 20050117974 | A | 12/2005 |
| KR | 200828029 | A | 3/2008 |
| KR | 20090027515 | A | 3/2009 |
| KR | 2009055309 | A | 6/2009 |
| RU | 2207111 | | 6/2003 |
| WO | WO01/17523 | A | 3/2001 |
| WO | WO2011/041648 | A1 | 4/2011 |

OTHER PUBLICATIONS

"Solvents". Internet Archive Date: Mar. 18, 2006 [Retrieved from the Internet on: Nov. 6, 2011]. Retrieved from the Internet: <URL: http://web.archive.org/web/20060318021311/http://www.chemical-land21.com/info/SOLVENTS.htm>.*

Sticher et al. "Phenolic Glycosides of Paulownia tomentosa Bark". Planta Med 1982; 46(11): 145-148.*

The AOCS Lipid Library. "Preparation of Lipid Extracts from Tissues". Retrieved from the Internet on: May 29, 2015. Retrieved from: <URL: http://lipidlibrary.aocs.org/topics/extract2/index.htm>.*

Plant Conservation Alliance's Alien Plant Working Group, Weeds Gone Wild: Alien Plant Invaders of Natural Areas, http:www.nps.gov/plants/alien/, Fact Sheet: Princess Tree, May 20, 2005, 1-3.

Preparation and RP-HPLC analysis of ursolic acid from Paulownia tomentosa (Thunb.) Steud leaves, Yi, Yanping et al., College of Chemistry and Bioengineering, Yichun University, Yichun, Jiangxi Province, Peop. Rep. China (2008), 19(4), 799-800. AN 2009:434345 CAPLUS.

(Continued)

*Primary Examiner* — Amy L Clark

(57) ABSTRACT

Provided are compositions comprising an extract of *Paulownia tomentosa* wood and methods of use thereof.

22 Claims, No Drawings

(56) References Cited

OTHER PUBLICATIONS

Bioassay guided fractionation of anthelminthic compounds from Paulownia tomentosa, Kehlbeck et al., Dept. of Chemistry, Union College, Schenectady, NY, USA, Abstracts of papers, 237th ACS National Meeting, Salt Lake City, UT, United States, Mar. 22-26, 2009. AN 2009:302719 CAPLUS.
Determination of flavonoids in the flowers of Paulownia tomentosa by high-performance liquid chromatography, Chen, et al., Key Laboratory for Natural Medicine of Gansu Province, Lanzhou Institute of Chemical Physics, Chinese Academy of Sciences, Peop. Rep. China, Journal of Analytical Chemistry (2009), 64(3), 282-288.AN 2009:300354 CAPLUS.
Studies on the phenylethanoid glycosides with anti-complement activity from *Paulownia tomentosa* var. *tomentosa* wood, Si et al., Tianjin Key Laboratory of Pulp & Paper, College of Material Science and Chemical Engineering, Journal of Asian Natural Products Research, Peop. Rep. China (2008), 10(11), 1003-1008. AN 2008:1423587 CAPLUS.
Preliminary study on the antioxidant activity of flavonoids from Paulownia tomentosa Steud flower, Meng et al., School of Chemistry and Chemical Engineering, Henan Institute of Science and Technology, Peop. Rep. China(2008), 25(5), 914-917. AN 2008:1353609 CAPLUS.
Cytotoxic activity of C-geranyl compounds from Paulownia tomentosa fruits, Smejkal, et al., Dept. of Natural Drugs, University of Veterinary and Pharmaceutical Sciences Brno, Czech Rep., Planta Medica (2008), 74(12), 1488-1491. AN 2008:1285586 CAPLUS.
Study on the stability of flavonoids from paulownia tomentosa stud flower, Meng et al., henan Institute of Science & Technology, School of Chemistry and Chemical Engineering, Peop. Rep. China (2008), 25(4), 655-658. AN 2008:1084661 CAPLUS.
Anti-Herbivore structures of paulownia tomentosa: morphology, distribution, chemical constituents and changes during shoot and leaf development, Kobayashi et la., Dept. of Bioscience and Biotechnology, Tokyo Institute of Technology, Tokyo, Japan; Annals of Botany (2008), 101(7), 1035-1047. Oxford University Press. An 2008:702202 CAPLUS.
Study on the content determination and extraction technology of total flavonoids from flowers of Paulownia tomentosa (Thunb) steud. Meng et al., Dept. of Chemistry and Chemical Engineering, Henan Institute of Science and Technology, Peop. Rep. China (2008), 25(2), 273-276. AN 2008:594498 CAPLUS.
Structure elucidation of phenylethanoid glycosides from *Paulownia tomentosa* Steud.var. *tomentosa* wood., Si et al., Tianjin Key Laboratory of Pulp and Paper, College of Material Science and Chemical Engineering, Tianjin University of Science and Technology, Peop. Rep. China (2008), 62(2), 197-200. AN 2008:308446 CAPLUS.
Geranylated flavanones from the secretion on the surface of the immature fruits of Paulownia tomentosa, Asai et al., Department of Chemistry and Materials Science, Graduate School of Science and Engineering, Tokyo Institute of Technology, Meguro, Tokyo, Japan, Phytochemistry (Elsevier) (2008), 69(5), 1234-1241.CAN 148:351349AN 2008:236100 CAPLUS.
Antibacterial C-Geranylflavonoids from Paulownia tomentosa Fruits, Smejkal et al., Department of NaturalDrugs, University of Veterinary and Pharmaceutical Sciences Brno, Brno, Czech Rep. Journal of Natural Products (2008), 71(4), 706-709. Publisher: American Chemical Society—American Society of Pharmacognosy, CODEN: JNPRDF ISSN: 0163-3864, CAN 148:398479 AN 2008:234427 CAPLUS.
Antibacterial phenylpropanoid glycosides from *Paulownia tomentosa* (Thunb.) Steud. var. *tomentosa* fruit, Si et al., Tianjin Key Laboratory of Pulp & Paper, Tianjin University of Science & Technology, Tianjin, Peop. Rep. China. Linchan Huaxue Yu Gongye (2007), 27(Suppl.), 37-40, CAN 148:466887 AN 2008:131742 CAPLUS.
Estimation and prediction on retention times of components from essential oil of Paulownia tonentosa flowers by molecular electronegativity-distance vector (MEDV), Liao et al., College of Chemistry and Chemical Engineering, Chongqing University, Chongqing, Peop. Rep. China, THEOCHEM (2008), 850(1-3),CAN 148:433205 AN 2008:82894 CAPLUS.
Antioxidant activity detection of 17 plant samples by using DPPH-method. Zhaoxiang; Tao et al., The Key Marine Biotechnology Laboratory, Huaihai Institute of Technology, Lianyungang, Peop. Rep. China. Shipin Keji (2006), (10), 264-268, Journal written in Chinese. CAN 148:444821 AN 2008:80216 CAPLUS.
Optimum extraction of ursolic acid in Paulownia tomentosa by orthogonal test. Zou, Sheng-qin et al. Key Laboratory of Jiangxi Province for Research on Active Ingredients in Natural Medicines, Bioengineering Research Institute of Yichun University, Yichun, Peop. Rep. China, Anjisuan He Shengwu Ziyuan (2007), 29(3), 51-53,65. 1006-8376. Journal written in Chinese. CAN 149:73127 AN 2007:1427851 CAPLUS.
HPLC determination of ursolic acid and oleanolic acid in Paulownia tomentosa (Thumb.) Steud by ultrasonic wave aided method. Liu et al., College of Chemistry and Bioengineering, Yichun University, Yichun, Peop. Rep. China. Guangdong Weiliang Yuansu Kexue (2007), 14(5), 19-22.. Journal written in Chinese. CAN 148:209222 AN 2007:1338423 CAPLUS.
Seasonal dynamics of four kinds of microelements in the leaf of Paulownia. Hu et al. Key Laboratory of Soil & Water Conservation and Desertification Combating, Ministry of Education, Beijing Forestry University, Beijing, Peop. Rep. China. Anhui Nongye Daxue Xuebao (2006), 33(3), 385-389. Journal written in Chinese. CAN 148:139640 AN 2007:1219250 CAPLUS.
Antiradical activity of Paulownia tomentosa (Scrophulariaceae) extracts.Smejkal et al. Natural Drugs Department, Faculty of Pharmacy, University of Veterinary and Pharmaceutical Sciences Brno, Brno, Czech Rep. Molecules (2007), 12(6), 1210-1219. Molecular Diversity Preservation International, 1420-3049, http:h'www.mdpi.org/molecules/papers/12061210.pdf Journal; Online Computer File written in English. CAN 147:134191 AN 2007:774578 CAPLUS.
Study of the antibacterial activity in vitro and determination of flavones of flos Paulowniae Wei, et al., School of Life Science, Shaanxi Normal University, Van, Peop. Rep. China, Tianran Chanwu Yanjiu Yu Kaifa (2006). 18(3), 401-404. Publisher: Tianran Chanwu Yanjiu Yu Kaifa Bianjibu, Journal written in Chinese. CAN 146:448693 AN 2007:357906 CAPLUS.
HPLC determination of ursolic acid in 30 kinds of natural plants in Jiangxi. Chen et al. Institute of Biology, Yichun University, Yichun, Jiangxi Province, Peop. Rep. China. Jiangxi Nongye Daxue Xuebao (2005), 27(1), 22-24, 51.: 1000-2286. Journal written in Chinese. CAN 143:465715 AN 2005:987558 CAPLUS.
Chemical composition of the essential oil from Paulownia tomentosa flowers, Wang, et al., Anal. and Test Cent., Shandong Acad. Sci., Jinan, Peop. Rep. China. Linchan HuaxueYu Gongye (2005), 25(2), 99-102. CAN 144:84067 AN 2005:604454 CAPLUS.
Isolation and structural elucidation of flavones from flower of Paulownia tomentosa, Du, et al., Lanzhou Institute of Chemical Physics, Chinese Academy of Sciences, Lanzhou, Gansu Province, Peop. Rep. China. Zhongcaoyao (2004), 35(3), 245-247. Journal written in Chinese. CAN 143:158880 AN 2005:306532CAPLUS
Synthesis of dihydroxyphenacyl glycosides for biological and medicinal study: 0-oxoacteoside from Paulownia tomentosa. Tozuka et al, The United Graduate School of Agricultural Science, Iwate University, Morioka, Japan. Journal of Wood Science (2005), 51(1), 48-59. Journal written in English. CAN 143:406056 AN 2005:261634 CAPLUS
HPLC determination of acteoside (verbascoside) in flowers of paulownia tomentosa (Thumb.) Steud. Chen, et al., Lanzhou Institute of Chemical Physics, Chinese Academy of Sciences, Lanzhou, Gansu Province, Peop. Rep. China, Yaowu Fenxi Zazhi (2004), 24(2), 123-125. Journal written in Chinese. CAN 142:417351 AN 2005:236829 CAPLUS
Analysis of volatile and semivolatile compounds of Paulownia tomentosa by gas chromatography coupled with mass spectrometry. Oprea, Eliza; Radulescu, Valeria; Chiliment, Silvia. Fac. Chim., Univ. Bucuresti, Bucharest, Rom. Revista de Chimie (Bucharest, Romania) (2004), 55(6), 410-412. Journal written in Romanian. CAN 142:204422 AN 2004:629656 CAPLUS

(56) References Cited

OTHER PUBLICATIONS

C-Geranyl Compounds from Paulownia tomentosa Fruits, Smejkal, et al., Department of Natural Drugs and Department of Chemical Drugs, University of Veterinary and Pharmaceutical Sciences Brno, Brno, Czech Rep.Journal of Natural Products (2007), 70(8), 1244-1248. Publisher: American Chemical Society—American Society of Pharmacognosy, CAN 147:318278 AN 2007:748581 CAPLUS.

Carbonic anhydrase activity and photosynthetic rate in the tree species *Paulownia tomentosa* Steud., Effect of dimethylsulfoxide treatment and zinc accumulation in leaves, Lazova, et al., Institute of Plant Physiology M. Popov, Bulgarian Academy of Sciences, Sofia, Bulg. Journal of Plant Physiology (2004), 161(3), 295-301. CAN 141:120393 AN 2004:349141.

Comparison of chemical components between fresh and dried-in-the-shade flowers of Paulownia tomentosa. Wang, et al., College of Chinese Pharmacy, Beijing University of Traditional Chinese Medicine, Beijing, Peep. Rep. China. Beijing Zhongyiyao Daxue Xuebao (2003), 26(3), 56-57. Journal written in Chinese. CAN 141:301124 AN 2004:230127 CAPLUS.

Study on the new extraction process of ursolic acid from the Paulownia tomentosa (Thunb.) Steud leaves, Han et al., Department of Chemical Engineering, Northwest University, Van, Peop. Rep. China. Xibei Daxue Xuebao, Ziran Kexueban (2003), 33(3), 304-306. Journal written in Chinese. CAN 140:231854 AN 2003:645555 CAPLUS.

A rapid method to establish suspension cultures of *Paulownia* species. Ho, et al., Division of Silviculture, Taiwan Forestry Research Institute, Taipei, Taiwan, Taiwan Linye Kexue (2002), 17(4), 421-427. Publisher: Taiwan Forestry Research Institute, CAN 139:175125 AN 2003:341361 CAPLUS.

Betaine distribution in the Scrophulariaceae and some previously included families, Blunden et al., School of Pharmacy and Biomedical Sciences, University of Portsmouth, Portsmouth, UK. Biochemical Systematics and Ecology (2003), 31(4), 359-365. CAN 139:66038 AN 2003:124889 CAPLUS.

Anticancer compound of Paulownia tomentosa. Moon et al., Pharmacognosy Laboratory, College of Pharmacy, Sung Kyun Kwan University, Suwon, S. Korea. Natural Product Sciences (2001), 7(1), 21-22. CAN 135:266816 AN 2001:473441 CAPLUS.

Protein diversity of Paulownia plant leaves and clusters, Fan et al., Institute of Panlownia, Henan Agricultural University, Zhengzhou, Peop. Rep. China. Journal of Forestry Research (English Edition) (2001), 12(1), 21-24. CAN 135:90004 AN 2001:350489 CAPLUS.

An antiviral furanoquinone from Paulownia tomentosa Steud. Kang et al., College of Pharmacy, Seoul National University, Seoul, S. Korea. Phytotherapy Research (1999), 13(7), 624-626. CAN 132:245884 AN 1999:797544 CAPLUS.

Separation of iridoid glucosides from Paulownia tomentosa using liquid chromatography, Kabzinski et al., Chromatography, Biochromatography, Environmental Analysis Lab., Univ. Lodz, Pol. American E Communications, Inc., CAN 131:2317 AN 1999:140586.

The application of reversed-phase high performance liquid chromatography method for identification of iridoid glucosides from Paulownia tomentosa (Thunb.) Steud., Kabzinski et al., Department of General Chemistry, Chromatography, Biochromatography and Environmental Analysis Laboratory, University of Lodz, Lodz, Pol. Herba Polonica (1997), 43(4), 437-441. CAN 129:51524 AN 1998:279665 CAPLUS.

Total synthesis of (+)-paulownin, Okazaki et al., Faculty Agric., Ehime Univ., Matsuyama, Japan. Bioscience, Biotechnology, and Biochemistry (1997), 61(4), 743-745,CAN 126:343422 AN 1997:308975 CAPLUS.

Distribution and seasonal variation in detection of phytoplasma in bark phloem tissues of single Pulownia trees infectd with witches broom, Sahashi et al., Tohoku res. Cent., For. For. Prod.Res. Inst., Morioka, Japan, Nippon Shokubutsu Byori Gakkaiho (1995), 61(5), 481-4. CAN 124:82375 AN 1995:970826 CAPLUS.

Distribution of flower color and anthocyanidin in Korean wild plants, Kim et al., Kwang Ja. College of Natural Resources, Yeungnam University, Kyongsan, S. Korea. Han'guk Wonye Hakhoechi (1996), 37(4), 582-587. Publisher: Korean Society for Horticultural Science, Journal written in Korean. CAN 125:322987 AN 1996:600276 CAPLUS.

Antibacterial phenylpropanoid glycosides from Paulownia tomentosa Steud., Kang, et al., Coll. Pharmacy, Seoul Natl. Univ., Seoul, S. Korea, Archives of Pharmacal Research (1994), 17(6), 470-5. CAN 122:286677 AN 1995:524754 CAPLUS.

Analysis of patterns of SOD isoenzyme and soluble proteins of Paulownia plants, Gong et al., Dep. Forestry, Huazhong Agricultural University, Wuhan, Peop. Rep. China, Huazhong Nongye Daxue Xuebao (1994), 13(5), 507-10. Journal written in Chinese. CAN 122:286674 AN 1995:519296 CAPLUS.

Tomentoside and 7-hydroxytomentoside, two iridoid glucosides from Paulownia tomentosa. Damtoft, Soeren; Jensen, Soeren Rosendal.Dep. Org. Chem., Tech. Univ. Denmark, Lyngby, Den. Phytochemistry (1993), 34(6), 1636-8. CAN 120:129515 AN 1994:129515 CAPLUS.

The chemistry of color changes in kiri wood (*Paulownia tomentosa* Steud.).III. A new caffeic acid sugar ester from kiri wood, Ota et al., 1993), 39(4), 479-85. CAN 119:273642 AN 1993:673642 CAPLUS.

Analytical characterization of new seed oils. Lotti, G. et al., Ist. Chim. Agrar, Univ. Pisa, Pisa, Italy. Rivista della Societa italiana di Scienza dell'Alimentazione (1985), 14(4), 263-70. CODEN: RSISAZ ISSN: 0391-4887. Journal written in Italian. CAN 104:203821 AN 1986:203821 CAPLUS.

Constituents of Paulownia tomentosa stem(III): the crystal structure of methyl 5-hydroxy-dinaphtho [1,2-2',3'] furan-7,12-dio ne-6-carboxyl ate. Park, 11 Yeong; Kim et al., Coll. Pharm., Seoul Natl. Univ., Seoul, S. Korea. Archives of Pharmacal Research (1992), 15(1), 52-7. CAN 117:208891 AN 1992:608891.

The chemistry of color changes in Kiri wood (*Paulownia tomentosa* Steud.) II. Radial distributions and seasonal variations of the contents of total phenolics, or caffeic acid sugar esters, and of Kiri peroxidase activity in the Xylem plus some properties of Kiri peroxidase, Ota et al., Fac. Agric., Iwate Univ., Morioka, Japan.Mokuzai Gakkaishi (1991), 37(3), 254-60. CAN 115:258493 AN 1991:658493 CAPLUS.

Chemical composition of Paulownia flowers. Song et al., Res. Inst. Chem. Process. Util. For. Prod., Chin. Acad. For., Nanjing, Peop. Rep. China, Linchan Huaxue Yu Gongye (1990), 10(4), 265-72. Journal written in Chinese. CAN 115:78593 AN 1991:478593 CAPLUS.

The chemistry of color changes in kiri wood (*Paulownia tomentosa* Steud). I. Caffeic acid sugar esters responsible for color changes. Ota et al., Fac. Agric., Iwate Univ., Morioka, Japan. Mokuzai Gakkaishi (1989), 35(5), 438-46. CAN 111:99173 AN 1989:499173 CAPLUS.

(+)-Piperitol from Paulownia tomentosa. Ina et al., Tokyo Coll. Pharm., Hachioji, Japan, Planta Medica (1987), ISSN: 0032-0943. Journal written in English.CAN 108:72133 CAPLUS.

Studies on the comprehensive utilization of various parts of the whole tree of Paulownia. f. Extraction and separation of saponins, flavones, alkaloids, paulowniaoside, paulownin and sesamin, Chen et al., Beijing For. Coll., Beijing, Peop. Rep. China. Beijing Linxueyuan Xuebao (1982), (3), 137- 40,1-plate Journal; General Review written in Chinese CAN98:2709 AN 1983:2709 CAPLUS.

Specific gravity, fiber length, and extractive content of young paulownia. Olson et al., Dep. For., Univ. Kentucky, Lexington, KY, USA. Wood and Fiber Science (1985), 17(4), 428-38. CAN 104:52238.

Chemistry and taxonomy of genus *Paulownia*. Padhye, P. M. et al., Sci., M. S. Univ. Baroda, India. Indian Botanical Reporter (1983), 2(2), 137-8. CAN 100:188802AN 1984:188802 CAPLUS.

Verbascoside and isoverbascoside from Paulownia tomentosa Steud. Schilling, et al., Org. Chem. Inst., Univ. Heidelberg, Heidelberg, Fed. Rep. Ger. Zeitschrift fuer Naturforschung, Ted B: Anorganische Chemie, Organische Chemie (1982), 37B(12), 1633-5. Journal written in German. CAN 98:86273 AN 1983:86273 CAPLUS.

Phenolic glycosides of Paulownia tomentosa bark. Sticher, O. et al., ETH-Zentr., Zurich, Switz., Planta Medica (1982), 46(3), 145-8 CAN 98:31424 AN 1983.31424 CAPLUS.

Isolation and characterization of paulownioside, a new highly oxygenated iridoid glucoside from Paulownia tomentosa. Adriani, et al.,

(56) References Cited

OTHER PUBLICATIONS

Claudio, Cent. Studio Chim. Sostanze Org. Nat., CNR, Rome, Italy, Journal of Natural Products (1981), 441,6), 739-44. CAN 96:118990 AN 1982:118990CAPLUS.
Studies on the constituents of flowers. VIII. On the components of the flower of Paulownia tomentosa Steudel. Kurihara et al., Tohoku Coll. Pharm., Sendai, Japan, Yakugaku Zasshi (1978), written in Japanese.
Isolation and characterization of syringyl component rich lignin. Yamasaki et al, Fac. Agric., Kagawa Univ., Miki, Japan, Holzforschung (1978), 32(2), 44-7. CAN 89:26302 AN 1978:426302 CAPLUS.
Constituents of medicinal plants, VIII. The stereochemistry of paulownin and isopaulownin. Takahashi, et al., Univ. Kanazawa, Japan.Chemical & Pharmaceutical Bulletin (1966), 14(6), 641-7. CAN 65:56761 AN 1966:456761 CAPLUS.
Constituents of Medicinal plants IV, Takahashi et al., Univ.Kanazawa Japan, Yakugaku Zasshi (1963), 83 1101-5. CAN 60:60841 AN 1964:60841 CAPLUS.
Constituents of medical plants. III. Constituents of leaves of Paulownia tomentosa and Rhododendron kaempferi. Tanabe, et al., Univ. Kanazawa, Japan. Kanazawa Daigaku Yakugakubu Kenkyu Nempo (1962), 12 7-14. Journal language unavailable. CAN 59:28740 AN 1963:428740 CAPLUS.
Search for new industrial oils. IV. Earle, et al., Northern Regional Research Lab., Peoria, IL, Journal of the American Oil Chemists' Society (1960), 37 440-7. Journal language unavailable. CAN 54:135538 AN 1960:135538CAPLUS.
Constituents of the bark of Paulownia tomentosa. Yoneichi, et al., (1959), 79 1226-8. Journal language unavailable. CAN 54:17726 AN 1960: CAPLUS.
Lignin and lignlfication. X. The isolation and characterization of the native lignin from kiri wood. De Stevens, et al., Fordham Univ., New York, NY, Journal of the American Chemical Society (1952), 74 3447-8. Journal language unavailable. CAN 47:49574 AN 1953:49574 CAPLUS.
Lignin. II. Lignin of Paulownia imperialis. Iwadare, Koiti. Nippon Kagaku Kaishi (1921-47) (1941), 62 186-9. From: Bull. Chem. Soc. Japan 16,150-4(1941) (in English). Journal language unavailable. CAN 36:15738 AN 1942:15738 CAPLUS.
Pharmacological action of Paulownia imperialis. Garello-Cantoni, A. Chimie et Industrie (Paris) (1937), 38 934.. Journal language unavailable. CAN 32:24860 AN 1938:24860 CAPLUS.
Pharmacological action of Paulownia imperialis, Garello-Cantbni, A., Atti soc sci. lett. Genova (1936), 1 182-8. Journal language unavailable. CAN 32:24859AN 1938:24859 CAPLUS.
Some Japanese Vegetable Oils. Imp. Univ. Tokyo, Journal of the College of Science, Imperial University of Tokyo (1909), Journal language unavailable. CAN 3:5925 AN 1909:5925 CAPLUS.
Phytochemical investigation of the fishing plant Verbascum sinuatum L. and some other Scrophulariaceae. [machine translation]. Rosenthaler, L. Pharm. Univ. Inst., Strassburg, Archiv der Pharmazie (Weinheim, Germany) (1902), 240 57-69. From: Chem. Zentr., 1902, I, 483.. Journal language unavailable. CAN 0:220106 AN 1906:220106 CAPLUS.
Phytochemical examination of verbascum sinuatum (used to poison fish) and some other scrophulariaceae. Rosenthaler, L. Archiv der Pharmazie (Weinheim, Germany) (1902), 240 57-69. From: J. Chem. Soc., Abstr. 82, II, 282-3 1902. Journal language unavailable.CAN 0:109102 AN 1906:109102 CAPLUS.
Studies on the phenylethanoid glycosides with anti-complement activity from *Paulownia tomentosa* var. *tomentosa* wood. Si Chuan-Ling et al., Tianjin Key Laboratory of Pulp & Paper, College of Material Science and Chemical Engineering, Tianjin University of Science and Technology, Tianjin, China. sichlii@tust.edu.cn ISSN:1028-6020. Journal; Article; (Journal Article); (Research Support, Non-U.S. Gov't) written in English. PubMed ID 19031237 AN 2008762702 MEDLINE.
Cytotoxic activity of C-geranyl compounds from Paulownia tomentosa fruits. Smejkal Karel et al., Department of Natural Drugs, University of Veterinary and Pharmaceutical Sciences Brno, Brno, Czech Republic, Planta medica (2008), 74(12), 1488-91. Journal code: 0066751. ISSN:0032-0943. MEDLINE.
Antibacterial C-geranylflavonoids from Paulownia tomentosa Fruits. Smejkal et al., Department of Natural Drugs, University of Veterinary and Pharmaceutical Sciences Brno, Palackeho 1-3, CZ-612 42 Brno, Czech Republic, Journal of natural products (2008), 71(4), 706-9. PubMed ID 18293924 AN 2008273065 MEDLINE.
Anti-herbivore structures of Paulownia tomentosa: morphology, distribution, chemical constituents and changes during shoot and leaf development.Kobayashi Sawa et al., Department of Bioscience and Biotechnology, Tokyo Institute of Technology, Meguro, Tokyo 152-8551, Japan, Annals of botany (2008), 101(7), 1035-47. PUBMED ID 18344545 AN 2008265090 MEDLINE.
Geranylated flavanones from the secretion on the surface of the immature fruits of Paulownia tomentosa. Asai Teigo et al., Department of Chemistry and Materials Science, Graduate School of Science and Engineering, Tokyo Institute of Technology, Meguro, Tokyo 152-8551, Japan, Phytochemistry (2008), 69(5), 1234-41. PubMed ID 18206191 AN 2008134990 MEDLINE.
Antiradical activity of Paulownia tomentosa (Scrophulariaceae) extracts. Srnejkal Karel et al., Natural Drugs Department, Faculty of Pharmacy, University of Veterinary and Pharmaceutical Sciences Brno, Palackeho 1-3, CZ-612 42 Brno, Czech Republic, Molecules (Basel, Switzerland) (2007), 12(6), 1210-9. Journal; Article; PubMed ID 17876290 AN 2007557129 MEDLINE.
Ando et al., Quasi-Drugs Developed in Japan for the Prevention or Treatment of Hyperpigmentary Disorders, Int. J. Mol. Sci. 2010, 11, 2566-2575.
Solano et al., Hypopigmenting agents: An updated review on biological, chemical and clinical aspects, Pigment Cell Res. 19; 550-571.
Volatile organic compounds from wood and their influences on the museum environment for preservation of artifacts, Oikawa, Tadashi, Cultural Department, Tohuku History Museum, Japan, Aroma Research (2009), 10(1), 30-34. Journal written in Japanese. AN 2009:378621 CAPLUS.
C-geranyl compounds from Paulownia tomentosa fruits, Smejkal et al., Department of Natural Drugs, University of Veterinary and Pharmaceutical Sciences Brno, Palackeho 1-3, CZ-612 42 Brno, Czech Republic. karel.mejkal@post.cz Journal of natural products (2007), 70(8), 1244-8. Journal; Article;.PubMed ID 17625893 AN 2007554981 MEDLINE.
Phenolic Glycosides of Paulownia tomentosa Bark. Sticher et al., Pharmazeutisches Institut, ETH-Zentrum, Zurich, Switzerland Planta medica (1982), 46(11), 145-8. PubMed ID 17396961 AN 2007196893 In-process for MEDLINE.
(+)-Piperitol from Paulownia tomentosa. Ina et al., Tokyo College of Pharmacy, 1432-1 Horinouchi, Hachioji, Tokyo 192-03, JapanPlanta medica (1987), 53(5), 504. PubMed ID 17269086 AN 2007063347 In-process for MEDLINE.
Carbonic anhydrase activity and photosynthetic rate in the tree species *Paulownia tomentosa* Steud. Effect of dimethylsulfoxide treatment and zinc accumulation in leaves. Lazova et al., Institute of Plant Physiology M. Popov-Sofia, Bulgarian Academy of Sciences, Acad. G. Bonchev Str., BI. 21, 1113 Sofia, Bulgaria, Journal of plant physiology (2004), 161(3), 295-301. PubMed ID 15077628 AN 2004181990 MEDLINE.
An antiviral furanoquinone from Paulownia tomentosa Steud. Kang et al., College of Pharmacy, Seoul National University, Seoul 151-742, Korea Phytotherapy research PTR (1999), 13(7), 624-6. PubMed ID 10548761 AN 2000018466MEDLINE
COLIPA Guideline: Guideline for the Colorimetric Determination of Skin Colour Typing and Prediction of the Minimal Erythemal Dose (Med) without UV Exposure, The European Cosmetic, Toiletry and Perfumery Association, Brussels 2007.
Antibacterial phenylpropanoid glycosides from Paulownia tomentosa Steud. Kang et al., College of Pharmacy, Seoul National University, Seoul, Korea Archives of pharmacal research (1994), 17(6), 470-5. PubMed ID 10319161 AN 1999252719 MEDLINE.
Antimicrobial activity of the epicarp of the fruits of Paulownia fortunei and Paulownia tomentosa. Cercos A P Laboratorios Pablo Zubizarreta Ward, Buenos Aires, Argentina Revista Argentina de microbiologia (1982), 14(2). 111-4, written in Spanish, PubMed ID 6821518 AN 1988218208 MEDLINE.

(56) References Cited

OTHER PUBLICATIONS

Studies on the constituents of flowers. VIII. On the components of the flower of Paulownia tomentosa Steudel (author's trans]). Kurihara et al., Journal of the Pharmaceutical Society of Japan (1978), 98(4), 541-4, written in Japanese. PubMed ID 660422 AN 1978196497MEDLINE.

Studies on constituents of medical plants. IV. chemical structure of paulownin, a component of wood of Paulownia tomentosa steud. takahashi et al., Journal of the Pharmaceutical Society of Japan (1963), 831101-5, written in Japanese. PubMed ID 14094204 AN 1964051881 MEDLINE.

Les glucides du Paulownia imperialis, holoside et heteroside. Chollet M M., Comptes rendus hebdomadaires des seances de l'Academie des sciences (1949), 228(5), 425-7, PubMed ID 18117813 AN 1949019409MEDLINE.

Zocchi, Skin Feel Agents, Handbook of Cosmetic Science and Technology, 35: 399-415 Marcel Dekker, Inc., NY 2001.

Oldenhove et al., Classification of Surfactants, Handbook of Cosmetic Science and Technology, 37: 431-450 Marcel Dekker, Inc., NY 2001.

Martin et al., Parthenolide-depleted Feverfew (*Tanacetum parthenium*) protects skin from UV irradiation and external aggression, Arch Dermatol Res. (2008) 300: 69-80.

Fisher et al., Molecular basis of sun-induced premature skin ageing and retinoid antagonism, Nature 379: 335-339 (1996).

G. J. Fisher, J. Invest. Dermatol. Symposium Proceedings. 14(1): 20-24 (2009).

J. Serup et al., Handbook of Non-Invasive Methods and the Skin, $2^{nd}$ eds., Ch 66.1 (1995).

Akerlof, Dielectric Constants of Some Organic Solcent-Water Mixtures at various Temperatures, JACS, vol. 54, No. 11, pp. 4125-4139 (Nov. 1932).

Angle, S. et al., "Stereoselective Synthesis of 3-Alkyl-2-aryltetrahydrofuran-4-ols: Total Synthesis of (±)-Paulownin", J. Org. Chem. 2008, 73, pp. 6268-6278.

"Cutaneous Skin Tags", Last review date: Nov. 12, 2009. [Retrieved from the Internet on: Nov. 16, 2011]. Retrieved from the Internet: ,URL: http://www.ncbi.nlm.hih.gov/pubmedhealth/PMH0001851/?report=printable>.

Hamamoto, Y. et al. "Inhibitory effect of azelastine, a potent antiallergic agent, on release of tumor necrosis factor-α from activated human peripheral blood mononuclear cells and U937 cells", Exp. Dermatol. 1993, 2, pp. 231-235.

Jeon et al., "Lotus (*Nelumbo nuficera*) flower essential oil increased melanogenesis in normal human melanocytes", Exp Mol Med. Jul. 31, 2009; 41(7): 517-524.

Kaufmann, B. et al., "Recent Extraction Techniques for Natural Products: Microwave-assisted Extraction and Pressurised Solvent Extraction", Phytochem. Anal. 2002, 13, pp. 105-113.

Li et al., "The Experiment Studies on Pharmcological Action of Paulownin", *Guangxi Sciences* (Apr. 2007). Abstract Only. Retreieved from the Internet: http://en.cnki.com.cn/Article_en/CJFDTOTAL-GXKK200704031.htm [Retrieved from the Internet on: Aug. 19, 2012].

Rossi et al., "Cellulite: a review", Journal of European Academy of Dermatology and Venereology (2000), pp. 251-262.

Xiaohui, P. et al., "Extracting Naphtha from Flower of Paulownia Tomentosa (Thunb) Steud", Journal of Ankang Teachers College, vol. 15, Dec. 31, 2003, English Abstract.

The Natural Beauty Workshop: Emulsion, The Magic Trick of Creams and Lotions, May 17, 2011.

International search report dated Mar. 21, 2013 for corresponding PCT/US2011/048077 application.

International search report dated Apr. 2, 2013 for corresponding PCT/US2011/048081 application.

International search report dated Feb. 28, 2013 for corresponding PCT/US2011/048085 application.

International search report dated Feb. 28, 2013 for corresponding PCT/US2011/048076 application.

International search report dated Feb. 6, 2013 for corresponding PCT/US2011/048073 application.

Yu Shaowen, Analysis of Paulownia elongate wood extract, Nov. 1, 1988, pp. 386-387.

Minina S.A., et al. Chemistry and Technology of Phytopreparations, M. GEOTAR Media, 2009, p. 82-97, English section only.

The AOCS Lipid Library. "Preparation of Lipid Extracts from Tissues". Retrieved from the internet on May 29, 2015. Retrieved from: <URL:http://lipidlibrary.aocs.org/topics/extract2/index.htm>.

Traditional Chinese Medicine Dictionary, edited by JiangSu New Medical School, Shanghai People's Publishing House, p. 1778-1779, ed. 1, published on Oct. 1977.

\* cited by examiner

COMPOSITIONS COMPRISING *PAULOWNIA TOMENTOSA* WOOD EXTRACTS AND USES THEREOF

FIELD OF INVENTION

The present invention relates to compositions comprising plant extracts for use on skin. More specifically, it relates to compositions comprising extracts of *Paulownia tomentosa* wood for a variety of uses on the skin.

DESCRIPTION OF RELATED ART

*Paulownia* is a genus of plants native to Asia which has spread gradually to Europe and the USA. Species from the *Paulownia* genus are generally considered ornamental trees with wide craft and ecological applications for their wood. For example, the wood of such trees is popular for making soundboards of stringed instruments in Japan, China, and Korea. It is also popular with timber merchants for use in making furniture. *Paulownia* trees have ecological uses and are considered phyto-remidiators, that is, they can process industrial contaminants through their vascular system to help clean and reclaim land.

In Japan, *Paulownia* is called kiri which refers specifically to one species, *Paulownia tomentosa*, also called "Princess Tree." Other names which are commonly used are "empress tree", "Foxglove Tree", "Royal Paulownia", "Pao tong" (in China) and "Odong-Namoo" (in Korea). The scientific name is "*Paulownia tomentosa*" with a number of synonyms reported in various literature, i.e. "*Paulownia imperialis*", "*Paulownia recurva*", and "*Bignonia tomentosa*". *Paulownia tomentosa* belongs to the family "Paulowniaceae" or sometimes refer to "Scrophulariaceae". The United States Department of Agriculture (plants.USDA.gov) Plant database identifies Princess tree by a unique symbol "PATO2", with *Paulownia tomentosa* and *Paulownia imperialis* as synonym names.

The flower oil of *Paulownia tomentosa* is well studied and found to be richer in aroma as compared to other species. A number of bioactivities are associated with extracts of various parts of *Paulownia*, e.g. anti-cancer components from flower extract, anthelminthic activity from non-specified extract, antibacterial activities from fruit and flower extracts, antioxidant activity from flower extract, and anti-viral properties from stem bark. Leaf extracts of *Paulownia* are described for hair growth and hair promoting properties.

The present invention relates to applicant's discovery that extracts of *Paulownia tomentosa* wood are beneficial for use in compositions on skin. For example, applicants have discovered that such compositions tend to exhibit significant and unexpected properties for skin including skin lightening, improving signs of aging, and reducing inflammation.

SUMMARY OF THE INVENTION

In one aspect, the present invention is directed to compositions comprising an extract of *Paulownia tomentosa* wood and a carrier.

In another aspect, the present invention is directed to methods of lightening the skin comprising the step of applying to skin in need of skin lightening treatment an extract of *Paulownia tomentosa* wood.

In another aspect, the present invention is directed to methods of improving a sign of aging in skin comprising the step of applying to skin in need of improving the signs of aging an extract of *Paulownia tomentosa* wood.

In yet another aspect, the present invention is directed to methods of reducing skin inflammation comprising the step of applying to a skin in need of reducing skin inflammation an extract of *Paulownia tomentosa* wood.

DESCRIPTION OF THE INVENTION

As noted above, applicants have discovered unexpectedly that extracts of the wood of *Paulownia tomentosa* may be used in compositions, preferably skin care compositions, and for methods of use including, but not limited to, skin lightening, improving signs of aging, and reducing inflammation.

As used herein, the term "lightening the skin" refers generally to lightening, brightening, whitening, and/or evening of the skin tone, skin color, and/or shade of skin, and/or to the reduction in sallowness, and/or to the lightening and/or fading of hyperpigmented marks and/or lesions including, but not limited to, pigmented spots, melanin spots, age spots, sun spots, senile lentigos, freckles, lentigos simplex, pigmented solar keratosis, seborrhoeic keratosis, melasma, acne marks, post-inflammatory hyperpigmentation, lentigines, ephelides, combinations of two or more thereof and the like. In certain embodiments, "lightening the skin" also refers to increased skin radiance, glow, translucency and/or luminescence and/or obtaining a more radiant, glowing, translucent or luminous skin tone appearance or a less yellow or sallow skin tone. In certain preferred embodiments, "lightening the skin" refers to lightening and evening the skin tone, increasing skin radiance and/or lightening age spots.

As used herein, the term "skin in need of skin lightening treatment" refers generally to skin that exhibits one or more property selected from the group consisting of: skin having a measured Individual Typology Angle (ITA) value below 41 as determined per the COLIPA GUIDELINE: GUIDELINE FOR THE COLORIMETRIC DETERMINATION OF SKIN COLOUR TYPING AND PREDICTION OF THE MINIMAL ERYTHEMAL DOSE (MED) WITHOUT UV EXPOSURE published in 2007, which is incorporated herein by reference and further described below, darkened and/or sallow skin, including skin darkened by UV, skin with uneven skin tone, or skin with one or more hyperpigmented marks and/or lesions including, but not limited to, pigmented spots, melanin spots, age spots, sun spots, senile lentigos, freckles, lentigos simplex, pigmented solar keratosis, seborrhoeic keratosis, melasma, acne marks, post-inflammatory hyperpigmentation, lentigines, ephelides, combinations of two or more thereof and the like. In the COLIPA guidelines, skin color is defined function of the ITA value as: very light skin >55; Light skin 41-55, Intermediate 28-41, and Tan skin <28. In certain preferred embodiments, "skin in need of skin lightening" refers to individuals with a skin having an ITA value of less than 41, such as about 40 or less, about 35 or less, about 30 or less, or more preferably about 28 or less. In certain other preferred embodiments, the present invention is directed to compositions and methods for use on skin in need of skin lightening treatment selected from sallow and/or darkened skin. In certain other preferred embodiments, the present invention is directed to compositions and methods for use on skin in need of skin lightening treatment selected from the group consisting of age spots, freckles, marks left after acne, and combinations of two or more thereof.

As used herein, "skin in need of improving the signs of aging" means a skin that is, but not limited to, sagging, loose, lax, rough, wrinkly, thinned, uneven. Improving the signs of aging means improving the firmness of the skin, improving the texture of the skin, improving the appearance of wrinkles in skin, improving the skin tone or the treatment of external aggressions in skin.

As used herein, "improving the firmness of skin" means the enhancing of the firmness or elasticity of the skin, preventing the loss of firmness or elasticity of skin, or preventing or treating sagging, lax and loose skin. The firmness or elasticity of the skin can be measured by use of a cutometer. See Handbook of Non-Invasive Methods and the Skin, eds. J. Serup, G. Jemec & G. Grove, Chapter 66.1 (2006). The loss of skin elasticity or firmness may be a result of a number of factors, including but not limited to aging, environmental damage, or the result of an application of a cosmetic to the skin.

As used herein, "improving the texture of skin" means the smoothing of the surface of the skin to remove either bumps or crevasses on the skin surface.

As used herein, "improving the appearance of wrinkles in skin" means preventing, retarding, arresting, or reversing the process of wrinkle and fine line formation in skin.

As used herein, "treatment of external aggressions in skin" means the reduction or prevention of the damage from external aggressions in skin. Examples of external aggressions include, but are not limited to, damage to the skin from the use of cleansers (e.g., topical cleansers containing surfactants), make-up, shaving as well as environmental damage such as from UV light (e.g., sundamage from sunlight or damage from non-natural sources such as UV lamps and solar simulators), ozone, exhaust, pollution, chlorine and chlorine containing compounds, and cigarette smoke. Effects of external aggressions on the skin include, but are not limited to, oxidative and/or nitrosative damage to and modifications on lipids, carbohydrates, peptides, proteins, nucleic acids, and vitamins. Effects of external aggressions on the skin also include, but are not limited to, loss of cell viability, loss or alteration of cell functions, and changes in gene and/or protein expression.

As used herein, "improving the skin tone" means the lightening of the appearance of the skin (e.g., lightening pigmented marks or lesions, reducing skin sallowness, and/or evening the color of the skin)

As used herein, "skin in need of reducing skin inflammation" means a skin exhibiting redness or erythema, edema, or being reactive or sensitive to external elements. External elements include, but are not limited to, sun rays (UV, visible, IR), microorganisms, atmospheric pollutants such as ozone, exhaust pollutants, chlorine and chlorine generating compounds, cigarette smoke, cold temperature, heat. Inflammatory disorders and related conditions which may be treated or prevented by use of the compositions of this invention include, but are not limited to the following: arthritis, bronchitis, contact dermatitis, atophic dermatitis, psoriasis, seborrheic dermatitis, eczema, allergic dermatitis, polymorphous light eruptions, inflammatory dermatoses, folliculitis, alopecia, poison ivy, insect bites, acne inflammation, irritation induced by extrinsic factors including, but not limited to, chemicals, trauma, pollutants (such as cigarette smoke) and sun exposure, secondary conditions resulting from inflammation including but not limited to xerosis, hyperkeratosis, pruritus, postinflammatory hyperpigmentation, scarring and the like. Preferably, the inflammatory disorders and related conditions which may be treated or prevented using the methods of the invention are arthritis, inflammatory dermatoses, contact dermatitis, allergic dermatitis, atopic dermatitis, polymorphous light eruptions, irritation, including erythema induced by extrinsic factors, acne inflammation, psoriasis, seborrheic dermatitis, eczema, poison ivy, insect bites, folliculitus, alopecia, and secondary conditions and the like.

As used herein, unless otherwise specified, all percentages of ingredients in compositions are weight percent of active/solids ingredient based on the total weight of composition.

As used herein, a composition that is "essentially free" of an ingredient means the composition that has about 2% or less of that ingredient by weight based on the total weight of the composition. Preferably, a composition that is essentially free of an ingredient has about 1% or less, more preferably about 0.5% or less, more preferably about 0.1% or less, more preferably about 0.05 or less, more preferably about 0.01% or less by weight based on the total weight of composition of the ingredient. In certain more preferred embodiments, a composition that is essentially free of an ingredient is free of the ingredient, i.e. has none of that ingredient in the composition.

As used herein, "cosmetically/dermatologically acceptable" means that the ingredients which the term describes are suitable for use in contact with tissues (e.g., the skin or hair) without undue toxicity, incompatibility, instability, irritation, allergic response, and the like.

Any suitable extracts of Paulownia tomentosa wood may be used in accord with the present invention. In general, the wood of the Paulownia tomentosa tree includes wood from the stem, branches, or a combination of both. Suitable extracts of Paulownia tomentosa wood may be derived from wood chips, wood dusts and/or small cuttings, and the like.

Suitable extracts of Paulownia tomentosa wood may be obtained using conventional methods including, but not limited to, direct extraction of material from the wood by grinding, macerating, pressing, squeezing, mashing, centrifuging, and/or processes such as cold percolation, agitation/distillation, microwave assisted extraction, sonication, supercritical/subcritical $CO_2$ compressed gas extraction with or without polar modifiers, pressurized solvent extraction, accelerated solvent extraction, pressurized or normal hot water extraction, surfactant assisted pressurized hot water extraction, oil extraction, membrane extraction, Soxhlet extraction, the gold finger distillation/extraction and/or processes disclosed, for example, in U.S. Pat. Nos. 7,442,391, 7,473,435, and 7,537,791 to Integrated Botanical Technologies, LLC, incorporated herein by reference, and the like, or by other methods such as solvent extraction, and the like. Any of a variety of solvents including polar solvents, non-polar solvents, or combinations of two or more thereof may be used in methods of comprising solvent extraction. Suitable polar solvents include polar inorganic solvents such as water and the like, polar organic solvents such as alcohols and corresponding organic acids, for example $C_1$-$C_8$ alcohols including methanol, ethanol, propanol, butanol, and the like and organic acids, including acetic acid, formic acid, propanoic acid, and the like, polyols and glycols, including $C_1$-$C_8$ polyols/glycols and the like, and combinations of two or more thereof. Suitable non-polar solvents include non-polar organic solvents such as alkanes, including $C_1$-$C_8$ alkanes, cycloalkanes, including $C_1$-$C_8$ alkanes, alkyl ethers, including $C_1$-$C_8$ alkyl ethers, Petroleum ethers, ketones, including $C_1$-$C_8$ ketones, methylene chloride, ethyl acetate, xylene, toluene, chloroform, vegetable oil, mineral oil and the like. In another embodiment extraction may be obtained by non-polar solvents described above or supercritical fluid extraction with or without a polar modifier such as $C_1$-$C_8$ alcohols, water, $C_1$-$C_8$ polyols/glycols or $C_1$-$C_8$ organic acids. In certain preferred embodiments, the extract of the invention is a polar extract prepared by pulverizing the wood and extracting using a polar solvent having a dielectric constant value of between 1 and 100 at 20° C., preferably a dielectric constant of a value between 4 and 60 at 20° C., more preferably a dielectric constant of a value between 4 and 50 at 20° C., and even more preferably a dielectric constant of a value between 4 and 40 at 20° C. Examples of preferred polar solvents include $C_1$-$C_8$ alcohols, $C_1$-$C_8$ polyols/glycols, $C_1$-$C_8$ organic acids, water and combinations of two or more thereof having a dielectric constant value of between 1 and 100, preferably between 4 and 60, and more preferably between 5 and 40 at 20° C., including, but not limited to, those solvents and combinations of solvents having the desired dielectric constant value as disclosed in "Dielectric Constants of Some Organic Solvent-Water Mixtures at Various Temperatures," Akerlof, Gosta; *JACS*, Vol. 54, No. 11 (November 1932), pp. 4125-4139, incorporated herein by reference. In certain preferred embodiments, the polar extract is extracted using one or more $C_1$-$C_8$ alcohols, $C_1$-$C_8$ polyols, $C_1$-$C_8$ glycols, and combinations of two or more thereof. In certain more preferred embodiments, the extract is extracted using one or more $C_1$-$C_4$ alcohols, $C_1$-$C_4$ polyols, and/or $C_1$-$C_4$ glycols. In certain more preferred embodiments, the extract is prepared using a solvent comprising methanol, ethanol, or a combination thereof with or without presence of water. In more preferred embodiment, the extract is prepared using anhydrous alcohol or reagent grade denatured alcohol and dried Kiri wood dust agitating at room temperature for 3 days. In certain preferred embodiments, the extract may be further refined by charcoal (also referred to as active carbon) treatment.

In certain embodiments, the *Paulownia tomentosa* extract may be prepared to be essentially free of certain materials. In one embodiment, the extract is essentially free of Ursolic acid, beta-Sitosterol, or both.

In certain embodiments, the composition may additionally include extracts from other parts of *Paulownia tomentosa*, for example, one or more of the bark, leaves, roots, fruits, seeds, or flowers. In other embodiments, the composition is essentially free from extracts of other non-wood parts of *Paulownia tomentosa*.

Any suitable amounts of *Paulownia tomentosa* wood extract may be used in the compositions of the present invention. Preferably, the compositions comprise a safe and effective amount of *Paulownia tomentosa* wood extract. As used herein, a "safe and effective amount" means an amount of the extract or of the composition sufficient to induce the desired effect, but low enough to avoid serious side effects, including cytotoxicity and the like. For embodiments comprising skin lightening uses of the composition, a "skin lightening effective amount" means an amount of extract that is effective to achieve a $\Delta L$ value that is greater than zero in the Skin Epidermal Equivalents Model as a skin Lightening Test ($\Delta L$) as described below. In certain preferred embodiments, the skin lightening effective amount is an amount effective to achieve a $\Delta L$ value of about 1 or greater.

For embodiments of the present invention related to uses of the compositions for improving a sign of aging in skin, an "effective amount for improving a sign of aging" means an amount that provides a percent inhibition of MMP-1 or MMP-9 production, measured in accord with the Inhibition of UV-Induced MMP induction procedure of Example 11 below, that is greater than zero. In certain preferred embodiments, the effective amount for improving a sign of aging is an amount that provides a percent inhibition of MMP-1 or MMP-9 production, measured in accord with the Inhibition of UV-Induced MMP induction procedure of Example 11 below, that is about 10% or greater.

For embodiments of the present invention related to uses of the compositions for reducing inflammation, an "effective amount for reducing inflammation" means an amount that provides a percent inhibition of skin inflammation (IL-8), measured in accord with the Anti-Inflammatory effects on Release of UV-Induced Pro-inflammatory mediators on Reconstituted Epidermis procedure for IL-8 of Example 7 below, that is greater than zero. In certain preferred embodiments, the effective amount for improving a sign of aging is an amount that provides a percent inhibition of skin inflammation (IL-8), measured in accord with the Anti-Inflammatory effects on Release of UV-Induced Pro-inflammatory mediators on Reconstituted Epidermis procedure for IL-8 of Example 7 below, that is about 10% or greater.

In certain preferred embodiments, the compositions comprise from greater than zero to about 20% *Paulownia tomentosa* wood extract. In certain other preferred embodiments, the compositions comprise from about 0.0001 to about 20%, from about 0.001 to about 10%, from about 0.01 to about 5%, from about 0.1 to about 5%, or from about 0.2 to about 2% *Paulownia tomentosa* wood extract. In certain other preferred embodiments, the compositions comprise from greater than zero to about 1%, from about 0.0001 to about 1%, from about 0.001 to about 1%, or from about 0.01 to about 1% *Paulownia tomentosa* wood extract. In certain other preferred embodiments, the compositions comprise from about 1 to about 5%, preferably from about 2 to about 5% *Paulownia tomentosa* wood extract.

Any suitable carrier may be used in the compositions of the present invention. Preferably, for a skin care composition, the carrier is a cosmetically-acceptable carrier. As will be recognized by those of skill in the art, cosmetically-acceptable carriers comprise carriers that are suitable for use in contact with the body, in particular the skin for skin whitening applications, without undue toxicity, incompatibility, instability, irritation, allergic response, and the like. A safe and effective amount of carrier is from about 50% to about 99.999%, preferably from about 80% to about 99.9%, more preferably from about 99.9% to about 95%, most preferably from about 99.8% to about 98% of the composition. The carrier can be in a wide variety of forms. For example, emulsion carriers, including, but not limited to, oil-in-water, water-in-oil, water-in-oil-in-water, and oil-in-water-in-silicone emulsions, are useful herein. These emulsions can cover a broad range of viscosities, e.g, from about 100 cps to about 200,000 cps. Examples of suitable cosmetically-acceptable carriers include cosmetically-acceptable solvents and materials for cosmetic solutions, suspensions, lotions, creams, serums, essences, gels, toners, sticks, sprays, ointments, liquid washes and soap bars, shampoos, hair conditioners, pastes, foams, mousses, powders, shaving creams, wipes, patches, strips, powered patches, microneedle patches, bandages, hydrogels, film-forming products, facial and skin masks, make-up, liquid drops, and the like. These product types may contain several types of cosmetically-acceptable carriers including, but not limited to solutions, suspensions, emulsions such as microemulsions and nanoemulsions, gels, solids, liposomes, other encapsulation technologies and the like. The following are non-limitative examples of such carriers. Other carriers can be formulated by those of ordinary skill in the art.

In one embodiment, the carrier contains water. In a further embodiment, the carrier may also contain one or more aqueous or organic solvents. Examples of organic solvents include, but are not limited to: dimethyl isosorbide; isopropylmyristate; surfactants of cationic, anionic and nonionic nature; vegetable oils; mineral oils; waxes; gums; synthetic and natural gelling agents; alkanols; glycols; and polyols. Examples of glycols include, but are not limited to, glycerin, propylene glycol, butylene glycol, pentalene glycol, hexylene glycol, polyethylene glycol, polypropylene glycol, diethylene glycol, triethylene glycol, capryl glycol, glycerol, butanediol and hexanetriol, and copolymers or mixtures thereof. Examples of alkanols include, but are not limited to, those having from about 2 carbon atoms to about 12 carbon atoms (e.g., from about 2 carbon atoms to about 4 carbon atoms), such as isopropanol and ethanol. Examples of polyols include, but are not limited to, those having from about 2 carbon atoms to about 15 carbon atoms (e.g., from about 2 carbon atoms to about 10 carbon atoms) such as propylene glycol. The organic solvents may be present in the carrier in an amount, based upon the total weight of the carrier, of from about 1 percent to about 99.99 percent (e.g., from about 20 percent to about 50 percent). Water may be present in the carrier (prior to use) in an amount, based upon the total weight of the carrier, of from about 5 percent to about 95 percent (e.g., from about 50 percent to about 90 percent). Solutions may contain any suitable amounts of solvent, including from about 40 to about 99.99%. Certain preferred solutions contain from about 50 to about 99.9%, from about 60 to about 99%, from about 70 to about 99%, from about 80 to about 99%, or from about 90 to 99%.

A lotion can be made from such a solution. Lotions typically contain at least one emollient in addition to a solvent. Lotions may comprise from about 1% to about 20% (e.g., from about 5% to about 10%) of an emollient(s) and from about 50% to about 90% (e.g., from about 60% to about 80%) of water.

Another type of product that may be formulated from a solution is a cream. A cream typically contains from about 5% to about 50% (e.g., from about 10% to about 20%) of an emollient(s) and from about 45% to about 85% (e.g., from about 50% to about 75%) of water.

Yet another type of product that may be formulated from a solution is an ointment. An ointment may contain a simple base of animal, vegetable, or synthetic oils or semi-solid hydrocarbons. An ointment may contain from about 2% to about 10% of an emollient(s) plus from about 0.1% to about 2% of a thickening agent(s).

The compositions useful in the present invention can also be formulated as emulsions. If the carrier is an emulsion, from about 1% to about 10% (e.g., from about 2% to about 5%) of the carrier contains an emulsifier(s). Emulsifiers may be non-ionic, anionic or cationic.

Lotions and creams can be formulated as emulsions. Typically such lotions contain from 0.5% to about 5% of an emulsifier(s), while such creams would typically contain from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type and water-in-oil type are well-known in the art and are useful in the subject invention. Multiphase emulsion compositions, such as the water-in-oil-in-water type or the oil-in-water-in-oil type, are also useful in the subject invention. In general, such single or multiphase emulsions contain water, emollients, and emulsifiers as essential ingredients.

The compositions of this invention can also be formulated as a gel (e.g., an aqueous, alcohol, alcohol/water, or oil gel using a suitable gelling agent(s)). Suitable gelling agents for aqueous and/or alcoholic gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically contains between about 0.1% and 5%, by weight, of such gelling agents.

The compositions of the present invention can also be formulated into a solid formulation (e.g., a wax-based stick, soap bar composition, powder, or wipe). The composition of the present invention can also be combined with a solid, semi-solid or dissolvable substrate (eg., a wipe, mask, pad, glove or strip).

The compositions of the present invention can also be formulated into formulation used for the oral cavity, such as toothpaste, gel, rinse, solution, patch, and the like. The compositions may also be formulated for use in the eye, such as in solutions, emulsions, suspensions used as drops or washes and the like, or formulated for use in the vaginal mucosa such as via gels, lotions, lubricants, and the like.

The compositions of the present invention may further comprise any of a variety of additional cosmetically active agents. Examples of suitable additional active agents include: additional skin lightening agents, darkening agents, additional anti-aging agents, tropoelastin promoters, collagen promoters, anti-acne agents, shine control agents, anti-microbial agents such as anti-yeast agents, anti-fungal, and anti-bacterial agents, anti-inflammatory agents, anti-parasite agents, external analgesics, sunscreens, photoprotectors, antioxidants, keratolytic agents, detergents/surfactants, moisturizers, nutrients, vitamins, energy enhancers, anti-perspiration agents, astringents, deodorants, hair removers, hair growth enhancing agents, hair growth delaying agents, firming agents, hydration boosters, efficacy boosters, anti-callous agents, agents for skin conditioning, anti-cellulite agents, fluorides, teeth whitening agents, anti-plaque agents, and plaque-dissolving agents, odor-control agents such as odor masking or pH-changing agents, and the like. Examples of various suitable additional cosmetically acceptable actives include hydroxy acids, benzoyl peroxide, D-panthenol, UV filters such as but not limited to avobenzone (Parsol 1789), bisdisulizole disodium (Neo Heliopan AP), diethylamino hydroxybenzoyl hexyl benzoate (Uvinul A Plus), ecamsule (Mexoryl SX), methyl anthranilate, 4-aminobenzoic acid (PABA), cinoxate, ethylhexyl triazone (Uvinul T 150), homosalate, 4-methylbenzylidene camphor (Parsol 5000), octyl methoxycinnamate (Octinoxate), octyl salicylate (Octisalate), padimate O (Escalol 507), phenylbenzimidazole sulfonic acid (Ensulizole), polysilicone-15 (Parsol SLX), trolamine salicylate, Bemotrizinol (Tinosorb S), benzophenones 1-12, dioxybenzone, drometrizole trisiloxane (Mexoryl XL), iscotrizinol (Uvasorb HEB), octocrylene, oxybenzone (Eusolex 4360), sulisobenzone, bisoctrizole (Tinosorb M), titanium dioxide, zinc oxide, carotenoids, free radical scavengers, spin traps, retinoids and retinoid precursors such as retinol, retinoic acid and retinol palmitate, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, peptides containing copper such as Cu:Gly-His-Lys, coenzyme Q10, amino acids such a proline, vitamins, lactobionic acid, acetyl-coenzyme A, niacin, riboflavin, thiamin, ribose, electron transporters such as NADH and FADH2, and other botanical extracts such as oat, aloe vera, Feverfew, Soy, Shiitake mushroom extracts, and derivatives and mixtures thereof.

In certain preferred embodiments, the compositions of the present invention are skin care compositions that comprise an extract of *Paulownia tomentosa* wood and at least one additional skin lightening active agent. Examples of suitable additional skin lightening active agents include, but are not limited to, tyrosinase inhibitors, melanin-degradation agents, melanosome transfer inhibiting agents including PAR-2 antagonists, exfoliants, sunscreens, retinoids, antioxidants, Tranexamic acid, tranexamic acid cetyl ester hydrochloride, skin bleaching agents, linoleic acid, adenosine monophosphate disodium salt, Chamomilla extract, allantoin, opacifiers, talcs and silicas, zinc salts, and the like, and other agents as described in Solano et al. Pigment Cell Res. 19 (550-571) and Ando et al. Int J Mol Sci 11 (2566-2575).

Examples of suitable tyrosinase inhibitors include but, are not limited to, Vitamin C and its derivatives, Vitamin E and its derivatives, Kojic Acid, Arbutin, resorcinols, hydroquinone, Flavones e.g. Licorice flavanoids, Licorice root extract, Mulberry root extract, Dioscorea Coposita root extract, Saxifraga extract and the like, Ellagic acid, Salicylates and derivatives, Glucosamine and derivatives, Fullerene, Hinokitiol, Dioic acid, Acetyl glucosamine, 5,5'-dipropyl-biphenyl-2,2'-diol (Magnolignan), 4-(4-hydroxyphenyl)-2-butanol (4-HPB), combinations of two or more thereof, and the like. Examples of vitamin C derivatives include, but are not limited to, ascorbic acid and salts, Ascorbic Acid-2-Glucoside, sodium ascorbyl phosphate, magnesium ascorbyl phosphate, and natural extract enriched in vitamin C. Examples of vitamin E derivatives include, but are not limited to, alpha-tocopherol, beta, tocopherol, gamma-tocopherol, delta-tocopherol, alpha-tocotrienol, beta-tocotrienol, gamma-tocotrienol, delta-tocotrienol and mixtures thereof, tocopherol acetate, tocopherol phosphate and natural extracts enriched in vitamin E derivatives. Examples of resorcinol derivatives include, but are not limited to, resorcinol, 4-substituted resorcinols like 4-alkyl-resorcinols such as 4-butyresorcinol (rucinol), 4-hexylresorcinol (Synovea HR, Sytheon), phenylethyl resorcinol (Symwhite, Symrise), 1-(2,4-dihydroxyphenyl)-3-(2,4-dimethoxy-3-methylphenyl)-Propane (nivitol, Unigen) and the like and natural extracts enriched in resorcinols. Examples of salicylates include, but are not limited to, 4-methoxy potassium salicylate, salicylic acid, acetylsalicylic acid, 4-methoxysalicylic acid and their salts. In certain preferred embodiments, the tyrosinase inhibitors include a 4-substituted resorcinol, a vitamin C derivative, or a vitamin E derivative. In more preferred embodiments, the tyrosinase inhibitor comprises Phenylethyl resorcinol, 4-hexyl resorcinol, or ascorbyl-2-glucoside.

Examples of suitable melanin-degradation agents include, but are not limited to, peroxides and enzymes such as peroxidases and ligninases. In certain preferred embodiments, the melanin-inhibiting agents include a peroxide or a ligninase.

Examples of suitable melanosome transfer inhibiting agents including PAR-2 antagonists such as soy trypsin inhibitor or Bowman-Birk Inhibitor, Vitamin B3 and derivatives such as Niacinamide, Essential soy, Whole Soy, Soy extract. In certain preferred embodiments, the melanosome transfer inhibiting agents includes a soy extract or niacinamide.

Examples of exfolliants include, but are not limited to, alpha-hydroxy acids such as lactic acid, glycolic acid, malic acid, tartaric acid, citric acid, or any combination of any of the foregoing, beta-hydroxy acids such as salicylic acid, polyhydroxy acids such as lactobionic acid and gluconic acid, and mechanical exfoliation such as microdermabrasion. In certain preferred embodiments, the exfoliant include glycolic acid or salicylic acid.

Examples of sunscreens include, but are not limited to, avobenzone (Parsol 1789), bisdisulizole disodium (Neo Heliopan AP), diethylamino hydroxybenzoyl hexyl benzoate (Uvinul A Plus), ecamsule (Mexoryl SX), methyl anthranilate, 4-aminobenzoic acid (PABA), cinoxate, ethylhexyl triazone (Uvinul T 150), homosalate, 4-methylbenzylidene camphor (Parsol 5000), octyl methoxycinnamate (Octinoxate), octyl salicylate (Octisalate), padimate O (Escalol 507), phenylbenzimidazole sulfonic acid (Ensulizole), polysilicone-15 (Parsol SLX), trolamine salicylate, Bemotrizinol (Tinosorb S), benzophenones 1-12, dioxybenzone, drometrizole trisiloxane (Mexoryl XL), iscotrizinol (Uvasorb HEB), octocrylene, oxybenzone (Eusolex 4360), sulisobenzone, bisoctrizole (Tinosorb M), titanium dioxide, zinc oxide, and the like.

Examples of retinoids include, but are not limited to, retinol (Vitamin A alcohol), retinal (Vitamin A aldehyde), retinyl acetate, retinyl propionate, retinyl linoleate, retinoic acid, retinyl palmitate, isotretinoin, tazarotene, bexarotene, Adapalene, combinations of two or more thereof and the like. In certain preferred embodiments, the retinoid is selected from the group consisting of retinol, retinal, retinyl acetate, retinyl propionate, retinyl linoleate, and combinations of two or more thereof. In certain more preferred embodiments, the retinoid is retinol.

Examples of antioxidants include, but are not limited to, water-soluble antioxidants such as sulfhydryl compounds and their derivatives (e.g., sodium metabisulfite and N-acetyl-cysteine, glutathione), lipoic acid and dihydrolipoic acid, stilbenoids such as resveratrol and derivatives, lactoferrin, iron and copper chelators and ascorbic acid and ascorbic acid derivatives (e.g., ascobyl-2-glucoside, ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinones. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, black tea, white tea, pine bark, feverfew, parthenolide-free feverfew, oat extracts, blackberry extract, cotinus extract, soy extract, pomelo extract, wheat germ extract, Hesperedin, Grape extract, Portulaca extract, Licochalcone, chalcone, 2,2'-dihydroxy chalcone, Primula extract, propolis, and the like.

The additional cosmetically active agent may be present in a composition in any suitable amount, for example, in an amount of from about 0.0001% to about 20% by weight of the composition, e.g., about 0.001% to about 10% such as about 0.01% to about 5%. In certain preferred embodiments, in an amount of 0.1% to 5% and in other preferred embodiments from 1% to 2%.

In certain preferred embodiments, the compositions of the present invention are skin care compositions that comprise an extract of *Paulownia tomentosa* wood and at least one additional anti-inflammatory agent. Suitable additional anti-inflammatory active agents include, but are not limited to, compounds that have an IC50 (concentration at which a compound achieves 50% inhibition of inflammation) of less than or equal to 100 µg/ml for Interleukin-2 in the ANTI-INFLAMMATORY ASSAY set forth below. In a preferred embodiment, the IC50 for the second anti-inflammatory compounds is less than about 70 µg/ml, more preferably less than about 50 µg/ml, more preferably less than about 40 µg/ml, more preferably less than about 30 µg/ml.

The ANTI-INFLAMMATORY ASSAY assesses the ability of an agent to reduce the production of cytokines by human lymphocytes stimulated with the T-cell receptor (TCR) activating agent phytohaemagglutinin (PHA), and is conducted in the following manner. Human leukocytes are collected from a healthy adult male via leukopheresis, and adjusted to a density of $1\times10^6$ cells/mL in serum free lymphocyte growth medium (ExVivo-15, Biowhittaker, Walkersville, Md.). PBLs are stimulated with 10 µg/mL PHA in the presence or absence of test samples following published methods (Hamamoto Y., et al. Exp Dermatol 2:231-235, 1993). Following a 48 hour incubation at 37° C. with 5% $CO_2$, the supernatant is removed and evaluated for cytokine content using commercially available multiplex cytokine detection kit.

Examples of suitable anti-inflammatory agents include substituted resorcinols, (E)-3-(4-methylphenylsulfonyl)-2-propenenitrile (such as "Bay 11-7082," commercially available from Sigma-Aldrich of St. Louis, Mo.), tetrahydrocurcuminoids (such as Tetrahydrocurcuminoid CG, available from Sabinsa Corporation of Piscataway, N.J.), extracts and materials derived from the following:

Phellodendron Amurense Cortex Extract (PCE)
Non-Denatured Soy (*Glycine max*)
Feverfew (*Tanacetum parthenium*)
Ginger (*Zingiber officinale*)
Ginko (*Ginko Biloba*)
Madecassoside (*centella asiatica* extract ingredient)
Cotinus (*Cotinus coggygria*)
Butterbur Extract (*Petasites hybridus*)
Goji Berry (*Lycium barbarum*)
Milk Thistle Extract (*Silybum marianum*))
Honeysuckle (*Lonicera japonica*)
Basalm of Peru (*Myroxylon pereirae*)
Sage (*Salvia officinalis*)
Cranberry Extract (*Vaccinium oxycoccos*)
Amaranth Oil (*Amaranthus cruentus*)
Pomegranate (*Punica granatum*)
Yerbe Mate (*Ilex paraguariensis* Leaf Extract)
White Lily Flower Extract (*Lilium Candidum*)
Olive Leaf Extract (*Olea europaea*)
Phloretin (apple extract)
Oat Flour (*Aveena Sativa*)
Lifenol (Hops: *Humulus lupulus*) Extract
Bugrane P (*Ononis spinosa*)
Licochalcone (Licorice: *Glycyrrhiza inflate* extract ingredient)
Symrelief (Bisabolol and Ginger extract) combinations of two or more thereof, and the like.

Resorcinol is a dihydroxy phenol compound (i.e., 1,3 dihydroxybenzene) having by the following structure:

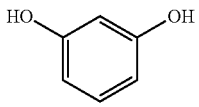

As used herein, "substituted resorcinol" means resorcinol comprising at least one substituent in the 2, 4, 5, or 6 position. Thus, the substituted resorcinol may have as few as one and as many as four substituents. Positions 1 and 3 of the substituted resorcinol comprise —OH groups, as shown above.

In embodiments wherein substituted resorcinol is used for anti-inflammation, it is highly preferred that all of the substituents of the substituted resorcinol are free of phenyl (—$C_6H_5$ aromatic) moieties. In certain embodiments, all of the substituents are free of aromatic moieties (with or without heteroatoms). In certain such embodiments, it is preferred that all of the substituents of the substituted resorcinol are free of ketone functionalities (carbonyls bonded to two other carbon atoms). In certain other such embodiments, all of the substituents of the substituted resorcinol are free of both phenyl functionalities and ketone functionalities. In certain other such embodiments, the substituted resorcinol comprises at least one substituent comprising 5 to 11 carbon atoms, preferably 5 to 10 carbon atoms, more preferably 5 to 9 carbon atoms, most preferably 5 to 8 carbon atoms. In certain other such embodiments, at least one substituent comprises an alkyl group, such as one having the number of carbon atoms described above. The alkyl group is preferably unsaturated.

In certain embodiments, the 4 position of the resorcinol is substituted, and, in certain embodiments, only the 4 position is substituted. In another embodiment, the 4 position is substituted with an alkyl group. In certain preferred embodiments, the substituted resorcinol comprises a single substituent at the 4 position that comprises an alkyl group. In certain other preferred embodiments, the substituted resorcinol comprises a single substituent at the 4 position that consists of an alkyl group directly bonded to the benzene ring.

Particularly suitable substituted resorcinols for anti-inflammation agents include 4-hexyl resorcinol and 4-octylresorcinol, particularly 4-hexyl resorcinol. The structures of 4-hexylresorcinol and 4-octylresorcinol are shown below:

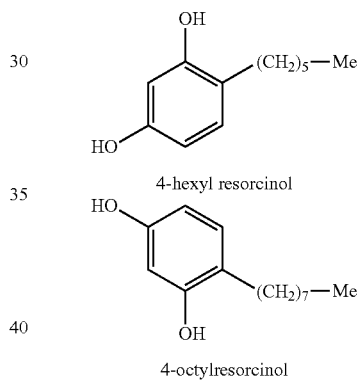

4-Hexyl resorcinol is commercially available as "SYNOVEA HR" from Sytheon of Lincoln Park, N.J. 4-Octylresorcinol is commercially available from City Chemical LLC of West Haven, Conn.

In certain embodiments, the substituted resorcinol comprises at least two substituents in the 2, 4, 5, or 6 positions. Such substituents may optionally be linked to form a ring, such as a cyclic aliphatic hydrocarbon optionally comprising heteroatoms such as sulfur or oxygen. Such a linked substituent may comprise 5 to 10 carbon atoms, e.g., 8 to 10 carbon atoms, and optionally include 1 to 3 heteroatoms. Examples of suitable substituted resorcinols comprising cyclic aliphatic substituents joining the 2 and 3 positions include Zearalanone and β-Zearalanol:

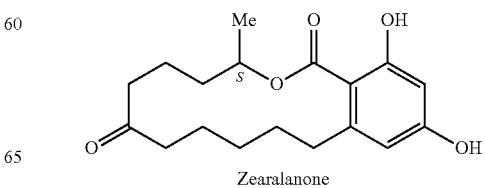

Zearalanone

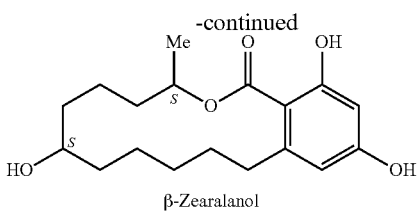

β-Zearalanol

Zearalanone and β-Zearalanol are commercially available from Sigma Chemicals of St. Louis, Mo.

In certain other embodiments, the substituted resorcinol comprises halide-containing and/or nitroso-containing substituents. Suitable examples contain —Cl or —N═O bonded directly to the benzene ring. These substituents may exist for example in the 2 and 4, 2 and 6, or 4 and 6 positions. An example of a dihalide-substituted resorcinol is 2,6-dichlororesorcinol. An example of a dinitroso-substituted resorcinol is 2,4-dinitrososorcinol:

2,4-dinitrososorcinol 2,6-Dichlororesorcinol and 2,4-Dinitrososorcinol are available from City Chemical LLC of West Haven, Conn.

Substituted resorcinols are prepared by means known in the art, for example, using techniques described in U.S. Pat. No. 4,337,370, the contents of which are incorporated herein by reference.

The substituted resorcinols may have any suitable molecular weight. In certain embodiments, the molecular weight of the substituted resorcinol ranges between about 175 and about 300.

By "extracts of feverfew," it is meant extracts of the plant "Tanacetum parthenium," such as may be produced according to the details set for the in U.S. Patent Application Publication No. 2007/0196523, entitled "PARTHENOLIDE FREE BIOACTIVE INGREDIENTS FROM FEVERFEW (TANACETUM PARTHENIUM) AND PROCESSES FOR THEIR PRODUCTION." One particularly suitable feverfew extract is commercially available as about 20% active feverfew, from Integrated Botanical Technologies of Ossining, N.Y.

Compositions of the present invention may include a cosmetically effective amount of one or more additional anti-inflammatory compounds. The compositions preferably include, on an active basis, from about 0.1% to about 10%, more preferably from about 0.5% to about 5%, of the additional anti-inflammatory compound.

In the inventive composition, the ratio of the concentrations of the Paulownia tomentosa wood extract to the additional anti-inflammatory compound may be varied. For example, the extract and the anti-inflammatory compound may be present in a concentration by weight ratio (which is determined by dividing the concentration by weight of the dry extract by the concentration by weight of the additional anti-inflammatory compound) of about 0.001 to about 100, preferably about 0.01 to about 10, more preferably about 0.25 to about 2.

In certain preferred embodiments, the compositions of the present invention are skin care compositions that comprise an extract of Paulownia tomentosa wood and at least one additional agent improving the signs of aging. Examples of suitable additional agents improving the signs of aging include, but are not limited to, tropoelastin promoters, collagen promoters, retinoids, hyaluronic acid, dimethylaminoethanol, N,N,N',N'-Tetrakis(2-hydroxypropyl)ethylenediamine, alpha hydrox acids, polyhydroxyacids, and combinations of two or more thereof.

"Tropoelastin promoter," as used herein, refers to a class of compounds that possess the biological activity of enhancing the production of tropoelastin. Tropoelastin promoters, according to the present invention, include all natural or synthetic compounds that are capable of enhancing the production of tropoelastin in the human body.

Suitable tropoelastin promoters may be determined, for example, using the TROPOELASTIN PROMOTER ASSAY. The TROPOELASTIN PROMOTER ASSAY is performed as follows. Rat cardiac myoblasts H9C2 (which may be purchased, for example from ATCC of Manassas, Va.) are used. Cultures are maintained in Dulbecco's modified Eagle's medium (DMEM, Invitrogen Life Technologies, Carlsbad, Calif.) supplemented with 10% fetal bovine serum, 2 mM glutamine, 100 units/ml penicillin, and 50 ug/ml streptomycin (Invitrogen LifeTechnologies, Carlsbad, Calif.). Cell cultures are transiently transfected with the elastin promoter-luciferase reporter construct (Elp2.2, a 2.2 kb elastin promoter fragment from nt −2267 to nt +2, driving the firefly luciferase gene, which may be obtained from Promega, Madison Wis.). DNA is prepared by Qiagen Maxi columns (Qiagen Valencia, Calif.). In all transfections, a construct with the thymidine kinase promoter and the Renilla luciferase reporter gene (pRL-TK, Promega, Madison Wis.) is included as an internal control. Typically, cells grown in 48-well plates are transfected with 0.45 ug total DNA per well using Lipofectamine 2000 (Invitrogen Life Technologies, Carlsbad, Calif.). One day after transfection, cells are treated with agents at indicated concentrations for approximately 24 hours before they are lysed for luciferase assays, using Dual-Luciferase Reporter System from Promega (Madison, Wis.), following manufacturer's protocol. The firefly luciferase activity is measured first (representing elastin promoter activity), followed by the renilla luciferase (internal control), using luminometer LMAX, from Molecular Devices (Sunnyvale, Calif.). The ratio of these two luciferase activities (RLU) is used to evaluate the Tropoelastin Promoter Activity. The tropoelastin promoter preferably has a Tropoelastin Promoter Activity of at least 1.1, preferably at least 1.25, more preferably at least 1.3, and most preferably at least 1.5, at at least one concentration in the range of 0.5 micrograms/milliliter to 2.5 milligrams per milliliter (on an actives basis), and preferably at at least one concentration in the range of 1.0 micrograms/milliliter to 2.5 milligrams per milliliter (on an actives basis).

Examples of suitable tropoelastin promoters include, but are not limited to, blackberry extracts, cotinus extracts, feverfew extracts, extracts of Phyllanthus niruri and bimetal complexes having copper and/or zinc constituents. The bimetal complex having copper and/or zinc constituents may be, for example, copper-zinc citrate, copper-zinc oxalate, copper-zinc tartarate, copper-zinc malate, copper-zinc succinate, copper-zinc malonate, copper-zinc maleate, copper-zinc aspartate, copper-zinc glutamate, copper-zinc glutarate, copper-zinc fumarate, copper-zinc glucarate, copperzinc polyacrylic acid, copper-zinc adipate, copper-zinc pimelate, copper-zinc suberate, copper-zinc azealate, copper-zinc sebacate, copper-zinc dodecanoate, or combinations thereof.

In a preferred embodiment, the tropoelastin promoter is selected from blackberry extracts, cotinus extracts, feverfew extracts, and combinations thereof. In a particularly preferred embodiment, the tropoelastin promoter is selected from blackberry extracts, feverfew extracts, and combinations thereof.

By "cotinus extract," it is meant an extract of the leaves of "*Cotinus coggygria*," such as a water extract thereof, available from Bilkokoop of Sofia, Bulgaria.

By "blackberry extract," it is meant a blend of compounds isolated from the plant of the genus *Rubus*, and preferably *Rubus fruticosus*. In one embodiment, the compounds are isolated from the flowers of the plant. In a further embodiment, the compounds are isolated from dried flowers of the plant. Such compounds may be isolated from one or more part of the plant (e.g., the whole plant, flower, seed, root, rhizome, stem, fruit and/or leaf of the plant). In a preferred embodiment, the blackberry extract is a blackberry leaf extract.

The extraction process may include by physically removing a piece of such plant, and, for example, grinding it. Further extraction of suitable compounds may also be isolated from the plant by using extraction procedures well known in the art (e.g., the use of organic solvents such as lower C1-C8 alcohols, C1-C8 alkyl polyols, C1-C8 alkyl ketones, C1-C8 alkyl ethers, acetic acid C1-C8 alkyl esters, and chloroform, and/or inorganic solvents such as water, inorganic acids such as hydrochloric acid, and inorganic bases such as sodium hydroxide).

For example, a blackberry leaf extract may be prepared by an extraction with water, alcohols such as ethanol or combination thereof as the solvent. However, an extract produced with a solvent including both ethanol and water is preferred. The blackberry leaves are preferably dried prior to extraction. It is also preferable to use only the leaves of the blackberry plant for the extraction and not also other plant parts such as the fruit (berries) of the blackberry or its branches and roots. In one embodiment, the extraction process for the production of a blackberry leaf extract comprises the following steps: a) addition to blackberry leaves of an solvent containing an alcohol selected from the group consisting of methanol, ethanol, npropanol, isopropanol, b) Extraction of the blackberry leaves with the solvent for up to 72 hours.

Detailed procedures for preparing a suitable blackberry leaf extract are disclosed in U.S. Patent Application Publication No. 2008/0095719, the disclosure of which is incorporated herein in its entirety.

One particularly suitable blackberry extract is produced by extracting the leaves of *Rubus fruticosus* with a mixture of water and ethanol compounded to an activity of about 5% to about 10%, with a maltodextrin matrix, commercially available from Symrise Inc. of Teterboro, N.J., and is sold under the name "SymMatrix."

Extracts of "*Phyllanthus niruri*" may be harvested and used as the whole plant, or optionally one or more parts of the plant (e.g., flower, seed, root, rhizome, stem, fruit and/or leaf of the plant) may be used. The *Phyllanthus niruri* plant or parts thereof may be finely divided, such as by grinding or milling, to a powder. A suitable milled form of *Phyllanthus niruri* is commercially available from Raintree Nutrition, Inc., of Carson City, Nev. Preferably, a low molecular weight fraction of *Phyllanthus niruri* is used, for instance a fraction of *Phyllanthus niruri* substantially free of molecular species having a molecular weight of greater than about 100,000 daltons. Preferably, such low molecular weight fraction is water extractable from the *Phyllanthus niruri* plant.

Compositions of the present invention may include a cosmetically effective amount of one or more tropoelastin promoters such as those described above. The compositions preferably include, on an active basis, from about 0.1% to about 10% of the tropoelastin promoters, more preferably from about 0.5% to about 5% of tropoelastin promoters, and most preferably from about 0.5% to about 2% of the tropoelastin promoters.

"Collagen promoter," as used herein, refers to compounds that possess the biological activity of enhancing the production of collagen. "Non-retinoid collagen promoters", according to the present invention, include all natural or synthetic compounds that are not retinoids, or derived from retinoids, and are capable of enhancing the production of collagen in the human body.

Suitable collagen promoters may be determined, for example, using the COLLAGEN PROMOTER ASSAY. The COLLAGEN PROMOTER ASSAY is performed as follows. Rat cardiac myoblasts H9C2, which may be purchased from ATCC (Manassas, Va.), are used. Cultures are maintained in Dulbecco's modified Eagle's medium (DMEM, Invitrogen Life Technologies, Carlsbad, Calif.) supplemented with 10% fetal bovine serum, 2 mM glutamine, 100 units/ml penicillin, and 50 ug/ml streptomycin (Invitrogen life technologies, Carlsbad, Calif.). Cell cultures are transiently transfected with the Collagen1A promoter-luciferase reporter construct, driving the firefly luciferase gene, which may obtained for example from PREMAS Biotech Pvt. Ltd (Haryana, India). In all transfections, a construct with the thymidine kinase promoter and the Renilla luciferase reporter gene (pRL-TK, Promega, Madison, Wis.) is included as an internal control. Cells grown in 48-well plates are transfected with 0.45 ug total DNA per well using Lipofectamine 2000 (Invitrogen life technologies, Carlsbad, Calif.). One day after transfection, cells are treated with agents at the indicated concentrations for approximately 24 hours before they are lysed for luciferase assays, using Dual-Luciferase Reporter System from Promega (Madison, Wis.), following manufacturer's protocol. The firefly luciferase activity is measured first (representing collagen promoter activity), followed by the renilla luciferase (internal control), using luminometer LMAX, from Molecular Devices (Sunnyvale, Calif.). The ratio of these two luciferase activities (RLU) is used to evaluate the activity of each promoter.

The suitable collagen promoter preferably has a Collagen Promoter Activity of at least 1.2, preferably at least 1.25, more preferably at least 1.3; at at least one concentration in the range of 0.5 micrograms/milliliter to 2.5 milligrams per milliliter (on an actives basis), preferably at at least one concentration in the range of 1.0 micrograms/milliliter to 2.5 milligrams per milliliter (on an actives basis).

Examples of suitable non-retinoid collagen promoters include, but are not limited to the following: extracts of feverfew (*Tanacetum parthenium*), extracts of *Centella asiatica*, extracts of *Siegesbeckia orientalis*; extracts of soy; collagen promoting peptides; ursolic acid; and asiaticoside.

*Centella asiatica*, also known as *Violette marronne* on Reunion Island, Gotu Kola or Indian pennywort in India, *Centella repanda* in North America, and Talapetraka in Madagascar, is a polymorphous herb and belongs to the family of *Umbelliferae* (Apiaceae), particularly to the *Hydrocotyle* subfamily. It grows wild throughout the tropics and prefers moist and shady regions at an altitude of about 600 to 1200 meters above sea level. *Centella asiatica* has three varieties: Typica, Abyssinica, and Floridana. The herb is known and used for its healing, sedative, analgesic, antidepressant, antiviral and antimicrobial properties. The biological activity of the herb appears to be due to the presence of triterpene molecules in the herb. A suitable extract of *Centella asiatica* is available as TECA from Bayer Consumer HealthCare of Basel, Switzerland.

By "extracts of *Siegesbeckia orientalis*," is meant any of various extracts of the plant *Siegesbeckia orientalis*, including Darutoside available from Sederma (Croda International Group of Edison, N.J.).

Suitable collagen-promoting peptides include the following:

(1) matrikine peptides, (i.e., a peptide derived from the degradation of extracellular matrix proteins—collagen, elastin, or proteoglycan) including palmitoyl pentapeptides, in particular Pal-Lys-Thr-Thr-Lys-Ser-OH, available as MATRIXYL from Sederma (Croda International Group of Edison, N.J.);

(2) GHK copper peptide available as PROCYTE from Photomedex of Montgomeryville, Pa.;

(3) Palmitoyl GHK peptide available as Biopoeptide CL from Sederma (Croda International Group of Edison, N.J.);

(4) Peptides VFTRN, TRNDKL disclosed in EP1775306 B1, and described below in the following formulas I, II and III:

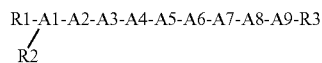
(I)

wherein formula I contains at least six amino acid residues; and:
A1 is Val, Ala, Leu, Met or absent;
A2 is Arg, Lys or absent;
A3 is Phe, Tyr or absent;
A4 is Thr, Ser, Ala, or Lys;
A5 is Arg or Lys;
A6 is Asn, Asp, Gly, or Gln;
A7 is Asp, Asn, Glu, or absent;
A8 is Lys, Arg or absent; and
A9 is Leu, Met, Val, Ile, Phe or absent;
provided that A3 may only be absent if A2 is absent, A2 may only be absent if A1 is absent, A7 may be absent only if A8 is absent, and A8 may only be absent if A9 is absent;
each R1 and R2, independently, is H, C1-12 alkyl, C7-10 phenylalkyl, or C(=O)E1, where E 1 is C1-12 alkyl, C3-14 alkenyl, C3-14 alkynyl, phenyl, 3,4-dihydroxyphenylalkyl, naphthyl, or C 7-10 phenylalkyl; provided that when either R1 or R2 is C(=O)E1, the other must be H; and
R3 is OH, NH2, C1-12 alkoxy, C7-10 phenylalkoxy, C11-14 naphthylalkoxy, C1-12 alkylamino, C7-10 phenylalkylamino, or C11-14 naphthylalkylamino; or a cosmetically acceptable salt thereof.

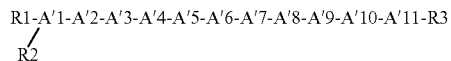
(II)

wherein formula II contains at least six amino acid residues; and:
A'1 is Val, Ala, Leu or Met;
A'2 is Arg or Lys;
A'3 is Phe or Tyr;
A'4 is Leu, Met, Val, Ile or Phe;
A'5 is His, Tyr or Phe;
A'6 is Ser, Thr, Ala or Lys;
A'7 is Tyr or Phe;
A'8 is Asp, Asn or Glu;
A'9 is Leu, Met, Val, Ile or Phe;
A'10 is Lys or Arg;
A'11 is Asn, Asp, Gly or Gln; and
R1, R2, and R3, are the same as those defined in formula I.

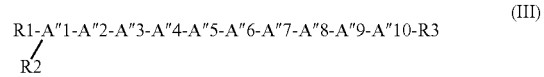
(III)

wherein formula III contains at least six amino acid residues; and:
A"1 is Cys or Ser;
A"2 is His, Tyr or Phe;
A"3 is Lys or Arg;
A"4 is Leu, Met, Val, Ile or Phe;
A"5 is Leu, Met, Val, Ile or Phe;
A"6 is His, Tyr or Phe;
A"7 is Asn, Asp, Gly or Gln;
A"8 is Val, Ala, Leu or Met;
A"9 is Asn, Asp, Gly or Gln;
A"10 is Lys or Arg; and
R1, R2, and R3, are the same as those defined in formula I.

(5) Biomimetic tetrapeptides, such as those available as Chronoline Tri Peptide from Unipex of Québec, Canada; and (6) Palmitoyl tri-peptide, available as Syn-Coll from DSM of Basel, Switzerland. Ursolic acid is also known as pentacyclic triterpene acid, Prunol, Malol, Urson, beta-ursolic acid and 3-Beta-Hydroxy-Urs-12-En-28-Oic Acid, It is commercially available for example from Sigma-Aldrich of St. Louis, Mo.

Asiaticoside, also known chemically as: [6[[3,4-dihydroxy-6-(hydroxymethyl)-5-(3,4,5-trihydroxy-6-methyloxan-2-yl)oxyoxan-2-yl]oxymethyl]-3,4,5-trihydroxyoxan-2-yl] 10,11-dihydroxy-9-(hydroxymethyl)-1,2,6a,6b,9,12a-hexamethyl-2,3,4,5,6,6a,7,8,8a,10,11,12,13,14b-tetradecahydro-1H-picene-4a-carboxylate) is commercially available for example from Bayer Santé Familiale Division Serdex, 69, Boulevard Victor Hugo 93400 SAINT-OUEN France.

Compositions of the present invention may include a cosmetically effective amount of one or more collagen promoters. The compositions preferably include, on an active basis, from about 0.1% to about 10% of the collagen promoters, more preferably from about 0.5% to about 5% of collagen promoters, and most preferably from about 0.5% to about 2% of the collagen promoters.

A variety of other materials may also be present in the compositions of the present invention. In certain preferred embodiments, the composition is a skin care composition comprising one or more materials selected from the group consisting of: surfactants, chelating agents, emollients, humectants, conditioners, preservatives, opacifiers, fragrances and the like.

What is meant by an emollient is a compound that helps to maintain the soft, smooth, and pliable appearance of the skin (e.g., by remaining on the skin surface or in the stratum corneum to act as a lubricant). Examples of suitable emollients include those found in Chapter 35, pages 399-415 (Skin Feel Agents, by G Zocchi) in Handbook of Cosmetic Science and Technology (edited by A. Barel, M. Paye and H. Maibach, Published in 2001 by Marcel Dekker, Inc New York, N.Y.), and include, but are not limited to, petrolatum, hexyldecyl stearate and plant, nut, and vegetable oils such as macadamia nut oil, rice bran oil, grape seed oil, palm oil, prim rose oil, hydrogenates peanut oil, and avocado oil.

What is meant by a humectant is a compound intended to increase the water content of the top layers of skin (e.g., hygroscopic compounds). Examples of suitable humectants include those found Chapter 35, pages 399-415 (Skin Feel Agents, by G Zocchi) in Handbook of Cosmetic Science and Technology (edited by A. Barel, M. Paye and H. Maibach, Published in 2001 by Marcel Dekker, Inc New York, N.Y.) and include, but are not limited to, glycerin, sorbitol or trehalose (e.g., α,α-trehalose, β,β-trehalose, α,β-trehalose) or a salt or ester thereof (e.g., trehalose 6-phosphate).

What is meant by a surfactant is a surface-active agent intended to cleanse or emulsify. Examples of suitable surfactants include those found in Chapter 37, pages 431-450 (Classification of surfactants, by L. Oldenhove de Guertechin) in Handbook of Cosmetic Science and Technology (edited by A. Barel, M. Paye and H. Maibach, Published in 2001 by Marcel Dekker, Inc New York, N.Y.) and include, but are not limited to anionic surfactants such as sulfates, cationic surfactants such as betaines, amphoteric surfactants such as sodium coco glycinate, noionic surfactants such as alkyl polygucosides.

Examples of suitable chelating agents include those which are capable of protecting and preserving the compositions of this invention. Preferably, the chelating agent is ethylenediamine tetracetic acid ("EDTA"), and more preferably is tetrasodium EDTA, available commercially from Dow Chemical Company of Midland, Mich. under the tradename, "Versene 100XL."

Suitable preservatives include, for example, parabens, quaternary ammonium species, phenoxyethanol, benzoates, DMDM hydantoin, organic acids and are present in the composition in an amount, based upon the total weight of the composition, from about 0 to about 1 percent or from about 0.05 percent to about 0.5 percent.

Any of a variety of conditioners which impart additional attributes, such as gloss to the hair are suitable for use in this invention. Examples include, but are not limited to, volatile silicone conditioning agent having an atmospheric pressure boiling point less than about 220° C. Examples of suitable volatile silicones nonexclusively include polydimethylsiloxane, polydimethylcyclosiloxane, hexamethyldisiloxane, cyclomethicone fluids such as polydimethylcyclosiloxane available commercially from Dow Corning Corporation of Midland, Mich. under the tradename, "DC-345" and mixtures thereof, and preferably include cyclomethicone fluids. Other suitable conditioners include cationic polymers, including polyquarterniums, cationic guar, and the like.

Any of a variety of commercially available pearlescent or opacifying agents are suitable for use in this invention. Examples of suitable pearlescent or opacifying agents include, but are not limited to, mono or diesters of (a) fatty acids having from about 16 to about 22 carbon atoms and (b) either ethylene or propylene glycol; mono or diesters of (a) fatty acids having from about 16 to about 22 carbon atoms (b) a polyalkylene glycol of the formula: HO-(JO)$_a$—H, wherein J is an alkylene group having from about 2 to about 3 carbon atoms; and a is 2 or 3; fatty alcohols containing from about 16 to about 22 carbon atoms; fatty esters of the formula: KCOOCH$_2$L, wherein K and L independently contain from about 15 to about 21 carbon atoms; inorganic solids insoluble in the shampoo composition, and mixtures thereof.

Any fragrance compositions suitable for use on skin and desirable for a skin care composition may be used in accord with the present invention.

In certain preferred embodiments, the present invention is in the form of a substrate comprising a composition of the present invention. Any suitable substrate may be used in the present invention. Examples of suitable substrates and substrate materials are disclosed, for example, in U.S. Published Application Nos. 2005/0226834 and 2009/0241242 which are incorporated herein by reference in their entirety.

In certain preferred embodiments, the substrate is a wipe, glove, or a facial mask. Preferably, such embodiments comprise a water-insoluble substrate as such is defined in the cited references above. For certain embodiments, the water-insoluble substrate may have a size and shape such that it covers the face of a human user to facilitate placing the water-insoluble substrate about the face of the user as a mask substrate. For example, the water-insoluble mask substrate may have openings for a mouth, nose, and/or eyes of the user. Alternatively, the water-insoluble substrate may have no such openings. Such a configuration without openings may be useful for embodiments of the invention in which the water-insoluble substrate is intended to be draped over a non-facial expanse of skin or if the water-insoluble substrate is intended to be used as wipe. The water-insoluble substrate may have various shapes, such as an angular shape (e.g., rectangular) or an arcuate shape such as circular or oval. For certain embodiments, the substrate is a glove such as described in U.S. Published Application No 2006/0141014 which is incorporated herein in its entirety.

In one embodiment of the invention, the product includes a plurality of water-insoluble substrates of different shapes. In one embodiment of the invention, the product includes a first water-insoluble substrate and a second water-insoluble substrate. The first water-insoluble substrate is shaped for application onto the forehead and the second water-insoluble substrate is shaped for application proximate to the mouth, such as areas above and/or below the lips, the chin, and/or the cheeks. In one embodiment of the invention, the first water-insoluble substrate is also applied to the nose region of the face. The first water-insoluble substrate may have a surface area of from about 100 cm$^2$ to about 200 cm$^2$, such as from about 120 cm$^2$ to about 160 cm$^2$ and the second water-insoluble substrate has a surface area of from about 100 cm$^2$ to about 300 cm$^2$, such as from about 150 cm$^2$ to about 250 cm$^2$. In one embodiment of the invention, the water-insoluble substrate has a low stiffness such that it may, for example, readily drape over or conform to the face or other body parts of the user.

The present invention further comprises methods of lightening the skin by applying to skin in need of skin lightening treatment an extract of *Paulownia tomentosa* wood, as such extracts and embodiments thereof are described above. In certain embodiments, the method comprises applying a composition of the present invention comprising an extract of *Paulownia tomentosa* wood, as such compositions are described above in various embodiments, to skin in need of skin lightening treatment.

The present invention may comprise application to any skin in need of treatment on the body. For example, application may be made to any one or more of the skin of the face, lips, neck, chest, back, arms, axilla, hands, feet and/or legs.

Preferably, the methods of the present invention comprise applying a skin lightening effective amount of of *Paulownia tomentosa* wood extract to the skin, preferably a safe and effective amount. In certain preferred embodiments, the methods comprise applying from greater than zero to about 20% *Paulownia tomentosa* wood extract to the skin in need. In certain other preferred embodiments, the methods comprise applying from about 0.0001 to about 20%, from about 0.001 to about 10%, from about 0.01 to about 5%, from about 0.1 to about 5%, or from about 0.2 to about 2% *Paulownia* tomentosa wood extract to the skin in need. In certain other preferred embodiments, the methods comprise from greater than zero to about 1%, from about 0.0001 to about 1%, from about 0.001 to about 1%, or from about 0.01 to about 1% *Paulownia tomentosa* wood extract to the skin. In certain other preferred embodiments, the methods comprise applying from about 1 to about 5%, preferably from about 2 to about 5% *Paulownia tomentosa* wood extract to the skin.

Any suitable method of applying the extract to the skin in need may be used in accord with the present invention. For example, the extract may be applied directly from a package to the skin in need, by hand to the skin in need, or may be transferred from a substrate such as a wipe or mask, or a combination of two or more thereof. In other embodiments, the extract may be applied via a dropper, tube, roller, spray, patch or added to a bath or otherwise to water to be applied to the skin, and the like.

In certain embodiments, the methods of the present invention further comprise the step of leaving the *Paulownia tomentosa* wood extract in contact with the skin for period of time. For example, in certain preferred embodiments after application, the extract is left in contact with the skin for a period of about 15 minutes or greater. In certain more preferred embodiments, the extract is left in contact with the skin for about 20 minutes or greater, more preferably about 1 hour or greater.

In certain embodiments, the method of the present invention comprises a regimen comprising applying the *Paulownia tomentosa* wood extract to skin multiple times over a selected period of time. For example, in certain embodiments, the present invention provides a method of skin lightening comprising applying to skin in need of skin lightening a composition comprising a *Paulownia tomentosa* wood extract once or twice daily for at least 12 weeks, preferably at least 8 weeks and more preferably for at least 2 weeks.

In certain preferred embodiments, the methods of the present invention comprise applying at least two different compositions or products comprising *Paulownia tomentosa* wood extract to the skin. For example, the methods may comprise applying a first composition comprising *Paulownia tomentosa* wood extract to skin in need of skin lightening followed by applying a second composition comprising *Paulownia tomentosa* wood extract, but that is otherwise different from the first composition, to the skin in need of skin lightening. In certain preferred embodiments, the first and second composition may be independently selected from the group consisting of lotions, cleansers, masks, wipes, creams, serums, gels, and the like. In certain preferred embodiments, at least one of the first and second compositions is a cleanser, lotion, cream, essence, or serum and the other is a facial mask or wipe. In certain other preferred embodiments, at least one of the first and second compositions is a cleanser and the other is a lotion or cream.

In certain other preferred embodiments, the method comprises applying at least three products comprising *Paulownia tomentosa* wood extract to skin in need of skin lightening. Preferably such three products are selected from the group consisting of cleansers, lotions, creams, essences, and facial masks.

The present invention further comprises methods of improving a sign of aging in skin comprising the step of applying to skin in need of improving the signs of aging an extract of *Paulownia tomentosa* wood as such extracts and compositions thereof are described above, as well as methods of reducing skin inflammation comprising the step of applying to a skin in need of reducing skin inflammation an extract of *Paulownia tomentosa* wood as such extracts and compositions thereof are described above.

The present invention may comprise application to any skin in need of treatment on the body. For example, application may be made to any one or more of the skin of the face, lips, neck, chest, back, arms, axilla, hands, feet and/or legs.

Preferably, the methods of the present invention comprise applying a safe and effective amount of of *Paulownia tomentosa* wood extract to the skin. In certain preferred embodiments, the methods comprise applying from greater than zero to about 20% *Paulownia tomentosa* wood extract to the skin in need. In certain other preferred embodiments, the methods comprise applying from about 0.0001 to about 20%, from about 0.001 to about 10%, from about 0.01 to about 5%, from about 0.1 to about 5%, or from about 0.2 to about 2% *Paulownia tomentosa* wood extract to the skin in need. In certain other preferred embodiments, the methods comprise from greater than zero to about 1%, from about 0.0001 to about 1%, from about 0.001 to about 1%, or from about 0.01 to about 1% *Paulownia tomentosa* wood extract to the skin. In certain other preferred embodiments, the methods comprise applying from about 1 to about 5, preferably from about 2 to about 5% *Paulownia tomentosa* wood extract to the skin.

Any suitable method of applying the extract to the skin in need may be used in accord with the present invention. For example, the extract may be applied directly from a package to the skin in need, by hand to the skin in need, or may be transferred from a substrate such as a wipe or mask, or a combination of two or more thereof. In other embodiments, the extract may be applied via a dropper, tube, roller, spray, patch or added to a bath or otherwise to water to be applied to the skin, and the like.

In certain embodiments, the methods of the present invention further comprise the step of leaving the *Paulownia tomentosa* wood extract in contact with the skin for period of time. For example, in certain preferred embodiments after application, the extract is left in contact with the skin for a period of about 15 minutes or greater. In certain more preferred embodiments, the extract is left in contact with the skin for about 20 minutes or greater, more preferably about 1 hour or greater.

In certain embodiments, the method of the present invention comprises a regimen comprising applying the *Paulownia tomentosa* wood extract to skin multiple times over a selected period of time. For example, in certain embodiments, the present invention provides a method comprising applying to skin in need a composition comprising a *Paulownia tomentosa* wood extract once or twice daily for at least 12 weeks, preferably at least 8 weeks and more preferably for at least 2 weeks.

In certain preferred embodiments, the methods of the present invention comprise applying at least two different compositions or products comprising *Paulownia tomentosa* wood extract to the skin. For example, the methods may comprise applying a first composition comprising *Paulownia tomentosa* wood extract to skin in need followed by applying to such skin a second composition comprising *Paulownia tomentosa* wood extract, but that is otherwise different from the first composition, to the skin in need.

The compositions of the present invention may be suitable for a variety of other uses. For example, compositions of the present invention may be useful for cleansing and/or moisturizing dry skin, treating signs of aging and/or for treating inflammation, including post-inflammatory hyperpigmentation, for reducing pore size, acne treatment, for reducing sebum production, for scar mitigation and reducing the appearance of stretch marks, for reducing the appearance of cellulite or orange peel appearance. In certain other embodiments, compositions of the present invention may be applied simultaneously with or within several hours of a mechanical or physical exfoliant such as a microdermabrasion treatment, or with a chemical exfoliant or keratolytic agent such as salicylic acid. In certain other embodiments, compositions of the present invention are applied to mucosa or other tissue such as vaginal, oral, or ocular tissue. In certain other embodiments, compositions of the present invention are applied to mild wounds or post-surgical sites to facilitate healing, to insect bites, to poison ivy or similar skin conditions, or in general to mitigate itch. In certain other embodiments, compositions of the present invention are applied to mitigate skin irritations. The irritation may be of external origins caused by ingredients in skin care and cosmetic products such as retinoid and its derivatives, benzyol peroxide, alpha-hydroxy acids and derivatives thereof, salicylic acid, surfactants, natural plant extracts, sunscreen actives, urea, and preservatives, etc. The irritation may be of other external origins such as the sun, wind, or shaving. The irritation may also be caused by inherent disease conditions such as acne, rosacea, atopic dermatitis, and other disease states. In other embodiments, compositions of the present invention may be useful to reduce redness of the gums. The extracts may further be suitable for use in reducing the appearance of telangiectasia or spider veins, reducing the appearance of rosacea, skin blotchiness, and skin blemishes. In certain embodiments, compositions of the present invention are applied to hair, scalp or both to improve hair health, quality and strength, to promote hair growth or retard hair loss, to prevent or treat dandruff, to prevent or treat seborrhea, seborrheic capitis and to improve scalp health and moisture. In other embodiments, compositions of the present invention are applied to the gum, in the mouth, to prevent or treat gum redness or irritation, to reduce periodontitis, to treat or prevent gingivitis, to reduce the symptoms or feeling of dry mouth. In yet other embodiments, the compositions of the present invention are applied to the eye to treat, prevent or reduce the appearance of red or irritated eye, to prevent or treat conjunctivitis, to improve eye moisture, to reduce the feeling of dry eye. In other embodiments, the compositions of the present invention are applied to the vaginal mucosa to prevent or treat signs of irritation or dryness, loss of firmness.

EXAMPLES

The following test methods were used in the Examples:
Melanin Synthesis Inhibition Test Control samples of B16(F10) murine melanoma cells were prepared and harvested as indicated below, but without addition of any test sample and without exposure to UVB (untreated control). Other control samples were prepared and harvested as indicated below without addition of test sample and exposed to UVB as described below (treated control). One or more samples of B16(F10) cells were prepared and each pre-treated with a test sample (e.g. E1) followed by UVB exposure as described below. Upon treatment, UVB stimulated melanogenesis in the cells and test compounds were evaluated based on their ability to inhibit or slow down the rate of melanogenesis. The cells were lysed for protein measurement at 595 nm and melanin content at 470 nm. The potency of the test compounds were determined by comparing the % inhibition achieved by the test compounds against the treated control.

Testing Procedure:

On a first day, murine melanoma B16(F10) cells were seeded in 60 mm plates with a density of ~1 million cells per plate and incubated for 48 hrs at 37° C., 5% $CO_2$. On day 2, the cells with a confluency rate of 90-100% were treated with test compound at a predetermined concentration (e.g. 25 µg/mL) for two hours (for test compound samples only) followed by exposure to UVB 200 mJ/cm$^2$ (for test samples and treated control). The cells were harvested on day 3 (24 h post UVB irradiation for test samples and treated control) and lysed in protein lysis buffer (50 mM Tris, pH 8, 2 mM EDTA, 150 mM NaCl, and 1% Triton X 100 —a nonionic surfactant purchased from BioRad Cat.#: 161-0407), and centrifuged. The resulting supernatant was mixed well with a protein dye assay (Bio-rad protein assay reagent) and a spectrophotometer (Molecular Devices VERSAmax) was used to determine the optical density (protein assay OD) of the sample at 595 nm. The cell pellet remaining after removal of the supernatant was dissolved in alkaline DMSO buffer, and the resulting solution used for melanin absorbance assay at 470 nm to determine melanin assay OD.

Three samples each of the untreated control, treated control, and each test sample were made and the Melanin and Protein OD measured for each. The normalized melanin for each untreated control (3 samples), treated control (3 samples) and test sample (3 samples for each test compound) was calculated via the following equation:

Normalized Melanin=melanin assay OD/protein assay OD.

The average normalized Melanin of the untreated controls was calculated (sum of the three calculated values/3), and the average normalized Melanin of the treated controls similarly calculated.

The Induction value of the Control was calculated via the equation:

Induction value of Control=average normalized Melanin of treated control−average normalized Melanin of untreated control.

The Induction value with each test sample is then calculated via the equation:

Induction value with Test Sample=normalized Melanin of the test sample−average normalized Melanin of untreated control.

The Inhibition % for each test sample is then calculated via the equation:

100×[(Induction value of Control−Induction value with Test Sample)/Induction value of Control].
The average Inhibition % is calculated as the sum of the three resulting Inhibition % values for each test sample divided by three.

The calculation sequence for % inhibition are explained by a theoretical example, see the following table.

| | |
|---|---|
| Average normalized melanin Untreated control | 0.98 |
| Average normalized melanin UVB treated control | 2.56 |
| Induction value of control | 2.56 − 0.98 = 1.58 |
| Average normalized melanin Test sample | 1.04 |
| Induction value with Test sample | 1.04 − 0.98 = 0.06 |
| Inhibition % for Test sample | [(1.58 − 0.06)/1.58] × 100 = 96.20% |

Skin Epidermal Equivalents Model as a skin Lightening Test (ΔL)

Skin epidermal equivalent tissues are available commercially from MatTek's MelanoDerm™ System and were used for the following tests. MatTek's MelanoDerm™ System consists of normal, human-derived epidermal keratinocytes (NHEK) and melanocytes (NHM) which have been cultured to form a multilayered, highly differentiated model of the human epidermis. Specifically, MEL-300-B tissues, each 9 mm in diameter were used in the following tests.

The test materials prepared in an appropriate vehicle and tested concentrations were applied topically to the skin model daily and the experiment lasted for 8 days. Measurement was taken on day 9.

The macroscopic and microscopic visual tissue darkening end points were measured by taking pictures with a digital camera. The Degree of Lightness for each tissue (L-Value) was measured using a spectrophotometer (Konica Minolta CM-2600d). The ΔL (degree of lightness as compared to control) for each test sample is calculated as per following formula:

$$\Delta L = L\text{-value of treated sample} - L\text{-value of control sample}.$$

Cell Viability Test

Cell Viability of the tissue during experiment was evaluated using the MTT assay described as follows. The MTT Tissue Viability Assay is a colorimetric assay system that measures the reduction of a yellow Methylthiazolyldiphenyl-tetrazolium bromide (MTT) into an insoluble purple product by the mitochondria of viable cells.

The skin epidermal tissues used previously to determine degree of lightness for each test material and of untreated tissues were used to determine percent viable cells remaining at the end of the experiment. The skin epidermal tissues after degree of lightnes test were incubated with MTT reagent for 3 h. After incubation extraction buffer is added to lyse the cells and allowed to continue overnight. Samples are read using a plate reader at a wavelength of 570 nm and compared against untreated control and expressed in % Cell Viability as of control. A reduction of ≥30% cell viability as of control consider as a significant indication of cell cytotoxicity caused by the test materials. The amount of purple color produced is directly proportional to the number of viable cells.

The following examples illustrates the preparation and efficacy of *Paulownia tomentosa* wood extracts.

Example 1

Four extracts, at least 20 mg each, of *Paulownia tomentosa* were obtained from Plant Extract Bank in Korea Research Institute of Biosciences & Biotechnologies representing combination of parts of the plant or individual parts of the plant. They were derived from: stem/bark/branches combination (E1), leaves (C1), bark (C2) and stem (E2). All of the extracts were prepared using Methanol under sonication at 50 deg C.

Example 2

The following example illustrates the preparation of *Paulownia tomentosa* wood extract (E3) in accord with certain embodiments of the present invention.

*Paulownia tomentosa* wood powder was obtained from Kurosawa Kiri Wood Supply Shop, Kitakata-city, Japan. Ten grams (10 g) of dry wood powder was suspended in 250 mL of reagent grade ethanol and stirred at room temperature for 72 h. The resulting suspension was filtered and the filtrate dried under low pressure using rotary evaporator at 30 deg C. Dry crude extract was obtained at 3.5% yield (350 mg). The crude extract was dissolved in methanol at a concentration of 1% and was treated with active carbon (700 mg) for 5 min at room temperature. Suspension filtered through 0.45 micron filter paper. The filtrate was dried to get a visibly lighter color material, E3, 210 mg (yields 60% from crude extract).

Example 3

The following example illustrates the preparation of *Paulownia tomentosa* wood extract (E4) that is essentially free of β-Sitosterol and Ursolic acid.

Deionized grade water (2.4 mL) was added to the *Paulownia tomentosa* stem/bark/branch extract (E1, 24 mg) from Example 1 above and sonicated for 5 min at room temperature. The resulting suspension was filtered through 0.45μ filter cartridge and the filtrate dried by freeze drying to obtain water soluble components (E4; 10.3 mg) at a yield of 43%. HPLC analysis shows the composition is essentially free from β-Sitosterol and Ursolic acid. No detectable amounts of either compounds are present in E4. The limit of detection (lod value) for β-sitosterol was 9 ppm (w/v) and for Ursolic acid was 0.5 ppm (w/v).

Example 4

The following example illustrates the skin lightening properties of *Paulownia tomentosa* extracts E1-E5 and comparative examples C1-C2.

All seven extracts were tested at different concentrations of up to 2% (as listed in Table 1) via the Skin Epidermal Equivalents Model as a skin Lightening Test (ΔL) as described above.

Cytotoxicity potential was determined by MTT assay for all extracts and calculated as % reduction of cell viability as compared to control, wherein >30% reduction of cell viability constitute significant cytotoxicity issues. The results are shown in Table 1 below.

A simple one-step extraction of the wood powder with just water as solvent at room temperature was also conducted (E5) and did not result in activity in the Skin Lightening Test. It is believed a more rigorous extraction (additional heat, agitation, etc.) may yield activity.

TABLE 1

Skin Lightening of extracts from parts of *Paulownia tomentosa* on 3D Skin Model

| Extract Code | Conc. (%) | Degree of Lightness (ΔL) | Std. Dev. |
|---|---|---|---|
| E1 | 1 | 2.86 | 0.44 |
|    | 2 | 3.48 | 0.19 |
| C1 | 1 | none | N/A |
|    | 2 | none | N/A |
| C2 | 1 | * | N/A |
|    | 2 | * | N/A |
| E2 | 1 | 2.48 | 0.69 |
|    | 2 | 3.71 | 0.43 |
| E3 | 0.5 | 1.2 | 0.34 |
|    | 1 | 1.91 | 0.32 |
|    | 2 | 4.11 | 0.17 |
| E4 | 2 | 2.97 | 0.25 |
| E5 | 1 | none | N/A |
|    | 2 | none | N/A |
|    | 5 | none | N/A |

* Represent significant cytotoxicity issues

Example 5

The following example illustrates the Melanin Synthesis Inhibition properties associated with *Paulownia tomentosa* wood extracts.

Stem/bark/branch extract (E1) and wood powder extract (E3) were tested for Melanogenesis Inhibition in accord with the Melanin Synthesis Inhibition Test described above and also for Tyrosinase inhibtition. The resulting measurements showed that the skin lightening effect of E1 & E3 were associated, at least in part, with Melanogenesis inhibition and not Tryosinase inhibition. The IC50 values of extracts E1 and E3 are 30 and 40 μg/mL for melanogenesis inhibition with no tyrosinase enzyme inhibition from either extracts.

Example 6

Anti-Inflammatory effects on Release of UV-Induced Pro-inflammatory mediators on Reconstituted Epidermis The effect of *Paulownia tomentosa* extract (E3) was evaluated for topical anti-inflammatory activity on human epidermal equivalents. Epidermal equivalents (EPI 200 HCF), multilayer and differentiated epidermis consisting of normal human epidermal keratinocytes, were purchased from MatTek (Ashland, Mass.). Upon receipt, epidermal equivalents were incubated for 24 hours at 37° C. in maintenance medium without hydrocortisone. Equivalents were topically treated (2 mg/cm$^2$) with *Paulownia tomentosa* extracts in 70% ethanol/30% propylene glycol vehicle 2 hours before exposure to solar ultraviolet light (1000 W-Oriel solar simulator equipped with a 1-mm Schott WG 320 filter; UV dose applied: 70 kJ/m$^2$ as measured at 360 nm). Equivalents were incubated for 24 hours at 37° C. with maintenance medium then supernatants were analyzed for IL-8 and IL-1α cytokine release using commercially available kits (Millipore Corp., Billerica, Mass.).

TABLE 2

| Treatment (Dose, as % w/v) | Mean of IL-8 Release (pg/mL) | Percent Inhibition of Skin Inflammation (over vehicle) |
| --- | --- | --- |
| Untreated, No UV | 170.79 | — |
| UV (60KJ) | 262.9 | — |
| UV (60KJ) + Vehicle (70:30 Ethanol:Propylene Glycol) | 253.8 | 0% |
| UV (60KJ) + *Paulownia tomentosa* extract 0.1% | 135.1 | 46.8% |
| UV (60KJ) + *Paulownia tomentosa* 5% | 125.9 | 50.3% |

TABLE 3

| Treatment (Dose, as % w/v) | Mean of IL-1α Release (pg/mL) | Percent Inhibition of Skin Inflammation (over vehicle) |
| --- | --- | --- |
| Untreated, No UV | 91.4 | — |
| UV (60KJ) | 188.7 | — |
| UV (60KJ) + Vehicle (70:30 Ethanol:Propylene Glycol) | 320.1 | 0% |
| UV (60KJ) + *Paulownia tomentosa* extract 0.1% | 161.2 | 55.2% |
| UV(60KJ) + *Paulownia tomentosa* extract 5% | 183.3 | 42.7% |

Based on the example above, topical application of the *Paulownia tomentosa* extract was able to significantly reduce the UV-stimulated release of inflammatory mediators. Therefore, *Paulownia tomentosa* extracts would be expected to provide an effective anti-inflammatory benefit when applied to skin.

Example 7

Inhibition of Reactive Oxygen Species Formation in Reconstituted Epidermis UV-induced hydrogen peroxide formation was determined using a modification of the method of Martin etal, *Arch Dermatol Res.* (2008) 300:69-80, in reconstituted epidermis and the human epithelial cell line, KB. Epidermal equivalents (EPI 200 HCF), multilayer and differentiated epidermis consisting of normal human epidermal keratinocytes, were purchased from MatTek (Ashland, Mass.). Upon receipt, epidermal equivalents were incubated for 24 hours at 37° C. in maintenance medium without hydrocortisone. After 24 hours, the tissues were incubated for 30 minutes with 5 μM of the hydrogen peroxide-sensitive fluorescent probe 5-(and-6)-chloromethyl-2',7'-dichlorodihydrofluorescein diacetate, acetyl ester (CM-H2DCFDA) (Invitrogen Corp., Carlsbad, Calif.). After incubation, the plate was rinsed to remove excess probe and equivalents were topically treated (2 mg/cm$^2$) with *Paulownia tomentosa* extract (E3) in 70% ethanol/30% propylene glycol vehicle. The plate was immediately read on a fluorescent plate reader set at wavelengths 485 nm excitation/530 nm emission to detect basal peroxide formation. The plate was then exposed to UV (1000 W-Oriel solar simulator equipped with a 1 mm Schott WG 320 filter; UV dose applied 4.2 kJ/m$^2$ as measured at 360 nm). The plate was read 60 minutes post UV exposure.

TABLE 4

| Treatment (Dose, as % w/v) | Mean Fluorescent Units | Percent Inhibition of ROS Production |
| --- | --- | --- |
| UV + Vehicle (70:30 Ethanol:Propylene Glycol) | 761.5 | 0% |
| UV + *Paulownia tomentosa* 0.1% | 361.4 | 52.5% |
| UV + *Paulownia tomentosa* 1.0% | 243.4 | 68.0 |
| UV + *Paulownia tomentosa* 5.0% | 261.9 | 65.6 |

Based on the example, topical application of *Paulownia tomentosa* extracts was able to significantly reduce the UV-stimulated production of ROS in reconstituted epidermis. Therefore when applied to skin, *Paulownia tomentosa* extracts would be expected to provide protection against induction of ROS from solar irradiation.

Example 8

Inhibition of UV-Induced MMP Induction

The ability of *Paulownia tomentosa* extract (E3) to inhibit UV induced matrix metalloproteinases-1 and -9 (MMP-1 and -9) was evaluated in epidermal equivalents derived from normal human epidermal keratinocytes. MMPs are a family of enzymes that play a major role in physiological remodeling and pathological destruction of extracellular matrix. It is well established that suberythemal doses of UV light induce MMP secretion in human skin, which in turn degrades the extracellular matrix and plays a significant role in photoaging wrinkle formation and loss of firmness and elasticity. See G. J. Fisher, et al., J Investig Dermatol. Symposium Proceedings. 14(1): 20-24 (2009).

In order to evaluate the ability of *Paulownia tomentosa* extracts to inhibit UV induced MMPs, epidermal equivalents (EPI 200 HCF), multilayer and differentiated epidermis consisting of normal human epidermal keratinocytes, were purchased from MatTek (Ashland, Mass.). Upon receipt, epidermal equivalents were incubated for 24 hours at 37° C. in maintenance medium without hydrocortisone. Equivalents were topically treated (2 mg/cm2) with *Paulownia tomentosa* extract (E3) in 70% ethanol/30% propylene glycol vehicle 2 hours before exposure to solar ultraviolet light (1000 W-Oriel solar simulator equipped with a 1-mm Schott WG 320 filter; UV dose applied: 70 kJ/m2 as measured at 360 nm). Equivalents were incubated for 48 hours at 37° C. with maintenance medium then supernatants were analyzed for MMP-1 and -9 using commercially available kits (R&D Systems, Minneapolis, Minn.). Data in Table 5 represents the mean of 2 independent experiments, each experimental condition is conducted using duplicate tissues.

TABLE 5

| Treatment (Dose, as % w/v) | Mean of MMP-1 Release (ng/ml) | Percent Inhibition of MMP-1 Production |
|---|---|---|
| UV + Vehicle (70:30 Ethanol:Propylene Glycol) | 12046.2 | 0% |
| UV + *Paulownia tomentosa* 0.1% | 5555.9 | 53.9% |
| UV + *Paulownia tomentosa* 1% | 4851.4 | 59.7% |
| UV + *Paulownia tomentosa* 5% | 4186.4 | 65.2% |

TABLE 6

| Treatment (Dose, as % w/v) | Mean of MMP-9 Release (ng/ml) | Percent Inhibition of MMP-9 Production |
|---|---|---|
| UV + Vehicle (70:30 Ethanol:Propylene Glycol) | 20795.5 | 0% |
| UV + *Paulownia tomentosa* 0.1% | 4585.9 | 77.9% |
| UV + *Paulownia tomentosa* 5% | 7077.2 | 65.9% |

Based on the example topical application of *Paulownia tomentosa* extract was able to significantly reduce the UV-stimulated release of MMP-1 and -9. Therefore when applied to skin, *Paulownia tomentosa* extracts would be expected to provide protection against induction of MMP-1 and -9 following solar irradiation.

Example 9

Inhibition of TNF-α-Induced MMP Induction

In order to evaluate the ability of *Paulownia tomentosa* extract (E3) to inhibit TNF-α induced MMPs, epidermal equivalents (EPI 200 HCF), multilayer and differentiated epidermis consisting of normal human epidermal keratinocytes, were purchased from MatTek (Ashland, Mass.). Upon receipt, epidermal equivalents were incubated for 24 hours at 37° C. in maintenance medium without hydrocortisone. Equivalents were topically treated (2 mg/cm2) with *Paulownia tomentosa* extract (E3) in 70% ethanol/30% propylene glycol vehicle 2 hours before treatment with TNF-α (100 ng/mL). Equivalents were incubated for 48 hours at 37° C. with maintenance medium then supernatants were analyzed for MMP-1 and -9 using commercially available kits (R&D Systems, Minneapolis, Minn.).

TABLE 7

| Treatment (Dose, as % w/v) | Mean of MMP-1 Release (ng/ml) | Percent Inhibition of MMP-1 Production |
|---|---|---|
| Untreated | 4848.4 | — |
| TNF-α induced | 7867.2 | 0% |
| TNF-α + *Paulownia tomentosa* 1% | 7225.2 | 0.8% |
| TNF-α + *Paulownia tomentosa* 5% | 5370.6 | 31.7% |

TABLE 8

| Treatment (Dose, as % w/v) | Mean of MMP-9 Release (ng/ml) | Percent Inhibition of MMP-9 Production |
|---|---|---|
| Untreated | 13217.6 | — |
| TNF-α induced | 42958.6 | 0% |
| TNF-α + *Paulownia tomentosa* 1% | 35145.3 | 18.2% |
| TNF-α + *Paulownia tomentosa* 5% | 16101.1 | 62.5% |

Based on the example topical application of *Paulownia tomentosa* extract was able to significantly reduce the TNF-α stimulated release of MMP-1 and -9. Therefore when applied to skin, *Paulownia tomentosa* extracts would be expected to provide protection against induction of MMP-1 and -9.

Example 10

The TROPOELASTIN PROMOTER ASSAY was performed using *Tanacetum parthenium* (parthenolide-free feverfew extract from Integrated Botanical Technologies of Ossining, N.Y.).

*Tanacetum parthenium* was diluted in cell culture media (DMEM Media of Invitrogen, San Diego Calif.) and *Paulownia tomentosa* was diluted in DMSO to the concentration of "active" indicated in Table 9 below. The compounds were added to the transfected H9c2 cells and were incubated for 24 hours. Test samples were compared to respective controls. The results are shown in Table 9 below.

TABLE 9

| Compound/Extract | Respective Concentrations of Actives (on active basis) | Normalized Tropoelastin Promoter Activity (RLU) | Percent change over respective controls | Ratio of NFκB-Inhibitor:Tropoelastin Promoter |
|---|---|---|---|---|
| Untreated control | — | 2.69 | — | |
| *Tanacetum parthenium* | 0.002% | 2.74 | 2% | |
| *Tanacetum parthenium* | 0.005% | 2.73 | 2% | |
| Vehicle control (DMSO) | 0.005% | 2.25 | — | |
| *Paulownia tomentosa* | 0.005% | 2.97 | 32% | |
| *Paulownia tomentosa* + *Tanacetum parthenium* | 0.005% + 0.002% | 3.48 | 55% | 2.5:1 |
| *Paulownia tomentosa* + *Tanacetum parthenium* | 0.005% + 0.005% | 3.64 | 62% | 1:1 |

As can be seen from the results shown in Table 9, *Paulownia tomentosa* and *Tanacetum parthenium* demonstrated percent changes in tropoelastin promotion over the respective controls of 32% and 2%, respectively. In contrast, the combination of both *Paulownia tomentosa* and *Tanacetum parthenium* demonstrated a 55% improvement in tropoelastin promotion over the vehicle control. This was much greater than a mere additive effect in performance.

A similar synergistic effect was observed when the concentration of *Tanacetum parthenium* was raised from 0.002% to 0.005%. *Tanacetum parthenium* at the higher concentration also showed a percent change in tropoelastin promotion over the control of 2%, whereas the combination of *Paulownia tomentosa* and *Tanacetum parthenium* achieved a percent change in tropoelastin promotion over the vehicle control of 62%.

The data demonstrates that the combination of *Paulownia tomentosa* and a tropoelastin promoter (*Tanacetum parthenium*) produces a surprising and synergistic increase in tropoelastin promotion activity.

Example 11

The following skin care composition was prepared using the ingredients shown in Table 10 in accord with the present invention.

TABLE 10

| Serial Number | Ingredient Trade Name | CTFA/INCI Name | Percentage in Formulation (w/w) |
|---|---|---|---|
| 1 | PURIFIED WATER | WATER | 59.69 |
| 2 | Ultrez 10 | Carbomer | 0.60 |
| 3 | VERSENE NA | Disodium EDTA | 0.20 |
| 4 | Brij 72 | Steareth-2 | 0.50 |
| 5 | Brij 721 | Steareth-21 | 1.00 |
| 6 | Finsolv TN | C12-15 Alkyl Benzoate | 2.00 |
| 7 | Miglyol 812 Neutral Oil | Caprylic/Capric triglyceride | 2.50 |
| 8 | Emery 917 | Glycerin | 3.00 |
| 9 | PENRECO SNOW WHITE | Petrolatum | 0.50 |
| 10 | Dimethicone | Dow Corning Q7-9120 Silicone Fluide (20 cst) | 2.00 |
| 11 | Phenonip XB | Methylparaben, ethyparaben, propylparaben, phenoxyethanol | 1.00 |
| 12 | Transcutol CG | EthoxyDiclycol | 5.00 |
| 13 | 1.0% Citric Acid | Citric acid | 0.01 |
| 14 | Princess Tree Extract | *Paulownia imperialis* Extract | 2.00 |
| 15 | Butylene Glycol | Butylene Glycol | 20.00 |
| 16 | SODIUM HYDROXIDE PELLETS (7680-88) NF FCC Pellets | Sodium Hydroxide | As needed |
|  |  | Total | 100.00 |

The above composition was prepared as follows: The purified water was added to a main tank at a temperature of 20-40° C. with smooth agitation. The Versene NA (disodium EDTA) was then added to the main tank. Agitation on the tank was stopped and Ultrez 10 (Carbomer) was added by evenly coating the top of the water mixture. The mixture was allowed to soak and agitation and heating was started. The mixture was heated and maintained at 55-60° C., and further mixed for 15 minutes or until homogeneous.

An oil phase was prepared by adding Finsolv TN (C12-15 alkyl benzoate) to a clean, suitable phase container with agitation and heating to achieve 55-60° C. After such temperature was achieved Brij 72 & 721 (Steareth-2, -21 resp.), Miglyol (Caprylic/Capric triglyceride), Emery 917 (glycerin), and Penreco snow white (Petrolatum) were added and mixed at 55-60° C. until addition to main tank.

The oil phase was added to the main tank with increased agitation and heating was stopped. The resulting mixture was mixed at high speed for 10-20 minutes. At 50° C. or lower, the Dimethicone (Dow Corning Silicone Fluid) was added. The batch mixture was then cooled to 40° C. and Phenonip XB (preservative mix) was added. The mixture was further mixed for 10 min or until uniform. Sodium hydroxide was added quickly (target pH=5.4) with further mixing for 10 minutes or until uniform pH is achieved.

An actives premix was made by adding Transcutol CG, Butylene glycol, Citric acid, and Princess Tree extract to a separate beaker and mixing well until uniform.

The final formulation was made by adding the actives premix to the main phase of the main tank, and mixing for an additional 10-20 minutes to dissolve completely or until uniform. The final volumes were made up with water, the formulation mixed for 10 minutes, and pH recorded.

The samples of composition were placed in 50° C. oven for 2 week and showed primary good stability.

Example 12

The following skin care composition was prepared using the ingredients shown in Table 11 in accord with the present invention.

TABLE 11

| Serial Number | CTFA/INCI Name | Percentage in Formulation (w/w) |
|---|---|---|
| 1 | Purified Water | 75.55 |
| 2 | Disodium EDTA | 0.15 |
| 3 | Ammonium Acryloyldimethyltaurate/VP Copolymer | 0.30 |
| 4 | Chlorphenesin C | 0.20 |
| 5 | Butylene glycol | 6.00 |
| 6 | Cetearyl Olivate/Sorbitan Olivate | 0.50 |
| 7 | Stearic Acid | 0.50 |
| 8 | Ethylhexylglycerin | 1.00 |
| 9 | Cyclopentasiloxne & Cyclohexasiloxane | 5.00 |
| 10 | Cyclopentasiloxane & Dimethicone Crosspolymer | 3.00 |
| 11 | Dimethiconol & Dimethicone | 2.00 |
| 12 | Sodium hydroxide | 2.40 |
| 13 | Polyacrylate 13 & Polyisobutene & Polysorbate 20 | 1.00 |
| 14 | Methylisothiazolinone | 0.15 |
| 15 | Fragrance | 0.01 |
| 16 | FD&C Red | 0.12 |
| 17 | D&C Yellow | 0.12 |
| 18 | *Paulownia imperialis* (Princess Tree) Extract | 2.00 |
|  | Total | 100.00 |

The above composition was prepared as follows: The purified water was added to a main tank followed by addition of disodium EDTA and mixed until the EDTA dissolved. Ammonium acryloyldimethyltaurate/VP Copolymer was sprinkled in and the resulting mixture heated to 70-75° C. After set temperature is achieved, Cetearyl Olivate/Sorbitan Olivate and Stearic acid were added while agitating the mixture for 5 minutes at set temperature.

An actives premix was prepared by dissolving Princess tree extract into butylene glycol at 40-50° C. in a separate container. Polyacrylate 13 and polyisobutene and polysorbate 20 were added to the Princess tree mix and then mixed until uniform. The temperature was lowered to 35-40° C. and set aside until ready to add to the main tank.

A Chlorophenesin premix was prepared by adding Chlorophehesin to butylenes glycol in a separate container and heating to 35° C., followed by addition of Methylisothiazolinone. The resulting mixture was heated to 50-55° C. and the temperature maintained until ready to mix into main tank.

An oil phase was prepared in a separate container by adding Cyclopentasiloxane and Dimethicone Crosspolymer to Cyclopentasiloxane and Cyclohexasiloxane while mixing and heating to 55-60° C. until uniform. Then Ethylhexylglycerin was added and mixed until uniform, followed by addition of Stearic acid with the temperature maintained between 55-60° C.

The oil phase was then added to the main tank slowly with vigorous agitation at a temperature of 70-75° C. Dimethiconol and dimethicone were added to the main batch and the resulting mixture stirred for 20 minutes or until uniform, after which the heating was stopped. The main pH was adjusted to between 5.0-5.5 with sodium hydroxide. The Chlorophenesin phase was added slowly at 50-55° C. while maintaining agitation. The mixture was cooled to 35-40° C. and the fragrance, FD&C red and D&C Yellow added and mixed well while maintaining the temperature.

The final formulation was achieved by adding the active premix to the main tank slowly with gentle mixing. The mixture was mixed for an additional 10-20 until uniform. The final volumes were made up with water, the formulation mixed for 10 minutes, and pH recorded.

The samples of composition were placed in 50° C. oven for 2 week and showed primary good stability.

What is claimed is:

1. A method of lightening human skin comprising topically applying to human skin in need of skin lightening an effective amount of a composition comprising from greater than zero to about 20% of a polar extract of *Paulownia tomentosa* wood, wherein said polar extract is obtained by extraction of *Paulownia tomentosa* wood with one or more solvents selected from the group consisting of: ethanol, methanol, or a combination thereof.

2. The method of claim 1, wherein said composition comprises from about 0.2% to about 2% of the polar extract of *Paulownia tomentosa* wood.

3. The method of claim 1, wherein said composition comprises from about 0.01% to about 5% of the polar extract of *Paulownia tomentosa* wood.

4. The method of claim 1, wherein said composition further comprises a carrier, and wherein said composition is in the form of: a solution, suspension, lotion, cream, serum, gel, stick, spray, ointment, liquid wash, soap bar, shampoo, hair conditioner, paste, foam, powder, mousse, shaving cream, hydrogel, or film-forming product.

5. The method of claim 4, wherein said composition is transferred from a substrate to the skin.

6. The method of claim 5, wherein said substrate is a wipe or facial mask.

7. The method of claim 1, wherein said composition further comprises an additional skin lightening active agent.

8. The method of claim 7, wherein said composition is transferred from a substrate to the skin.

9. The method of claim 8, wherein said substrate is a wipe or facial mask.

10. The method of claim 1, wherein said composition comprising the polar extract of *Paulownia tomentosa* wood is applied once or twice daily for at least 2 weeks.

11. The method of claim 1, wherein said composition comprising the polar extract of *Paulownia tomentosa* wood is in the form of two or more different compositions.

12. The method of claim 11, wherein said two or more different compositions comprising the polar extract of *Paulownia tomentosa* wood are are selected from the group consisting of: lotions, cleansers, masks, essences, wipes, creams, serums, gels, and combinations thereof.

13. The method of claim 12, wherein one of said two or more different compositions is in the form of a cleanser and another of said two or more different compositions is in the form of a lotion or cream.

14. The method of claim 12, wherein said two or more different compositions comprising the polar extract of *Paulownia tomentosa* wood are at least three different compositions, and wherein said at least three compositions are selected from the group consisting of: cleansers, lotions, creams, essences, facial masks and combinations thereof.

15. The method of claim 1, wherein said human skin in need of skin lightening treatment is selected from the group consisting of: skin darkened by UV, skin with uneven skin tone, skin having one or more pigmented spots, melanin spots, age spots, sun spots, senile lentigos, freckles, lentigos simplex, pigmented solar keratosis, seborrhoeic keratosis, melasma, acne marks, and combinations of two or more thereof.

16. The method of claim 15, wherein said human skin in need of skin lightening treatment is selected from the group consisting of: skin having one or more pigmented spots, melanin spots, age spots, sun spots, freckles, acne marks, and combinations of two or more thereof.

17. The method of claim 1, wherein said polar extract of *Paulownia tomentosa* wood is essentially free from extracts of non-wood parts of *Paulownia tomentosa*.

18. The method of claim 17, wherein said polar extract of *Paulownia tomentosa* wood is essentially free from extracts of leaves and bark of *Paulownia tomentosa*.

19. The method of claim 1, wherein said polar extract of *Paulownia tomentosa* wood is essentially free of ursolic acid, beta-sitosterol, or both.

20. A method of lightening human skin comprising topically applying to human skin in need of skin lightening an effective amount of a composition comprising from about 0.2% to about 2% of a polar extract of *Paulownia tomentosa* wood, wherein said polar extract is essentially free of ursolic acid, beta-sitosterol, or both, and wherein said polar extract of *Paulownia tomentosa* wood is obtained by extraction with ethanol, methanol, or a combination thereof.

21. The method of claim 20, wherein said polar extract of *Paulownia tomentosa* wood is essentially free from extracts of non-wood parts of *Paulownia tomentosa*.

22. The method of claim 21, wherein said polar extract of *Paulownia tomentosa* wood is essentially free from extracts of bark and leaves of *Paulownia tomentosa*.

* * * * *